US 6,737,431 B2

(12) United States Patent
Takaki et al.

(10) Patent No.: US 6,737,431 B2
(45) Date of Patent: May 18, 2004

(54) BENZOXAZOLE DERIVATIVES AS NOVEL MELATONERGIC AGENTS

(75) Inventors: Katherine S. Takaki, Middletown, CT (US); Li-Qiang Sun, Glastonbury, CT (US); Graham Johnson, Madison, CT (US); Stephen R. Bertenshaw, Cheshire, CT (US); Derek Denhart, Durham, CT (US); Jie Chen, Madison, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/383,131

(22) Filed: Mar. 6, 2003

(65) Prior Publication Data
US 2003/0216456 A1 Nov. 20, 2003

Related U.S. Application Data

(60) Provisional application No. 60/363,817, filed on Mar. 12, 2002.

(51) Int. Cl.$^7$ ............... A61K 31/423; A61P 25/24; C07D 263/56; C07D 263/57
(52) U.S. Cl. ............... 514/375; 548/217; 548/224
(58) Field of Search ............... 548/217, 224; 514/375

(56) References Cited

U.S. PATENT DOCUMENTS

| 5,276,051 A | 1/1994 | Lesieur et al. |
| 5,308,866 A | 5/1994 | Lesieur et al. |
| 5,380,750 A | 1/1995 | Lesieur et al. |
| 5,621,142 A | 4/1997 | Mochizuki et al. |
| 5,753,709 A | 5/1998 | Keavy et al. |
| 5,856,529 A | 1/1999 | Catt et al. |
| 6,211,225 B1 | 4/2001 | Takaki et al. |

FOREIGN PATENT DOCUMENTS

| EP | 0 527 687 | 2/1993 |
| WO | WO 94/07487 | 4/1994 |
| WO | WO 95/22521 | 8/1995 |

OTHER PUBLICATIONS

Yous, etal, *Chemical Abstracts*, vol. 134, No. 366, 826 (2001).*

Arendt, J., et al., "Alleviation of Jet Lag by Melatonin: Preliminary Results of Controlled Double Blind Trial", *Br. Med. J.*, 292, pp. 1170 (May 1986).

Cassone, V. M., et al., "Dose–Dependent Entrainment of Rat Circadian Rhythms by Daily Injection of Melatonin", *J. Biol. Rhythms*, 1(3), pp. 219–229 (1986).

* cited by examiner

*Primary Examiner*—Robert W. Ramsuer
(74) *Attorney, Agent, or Firm*—Aldo A. Algieri

(57) ABSTRACT

Novel benzoxazole derivatives which have a binding affinity for the human melatonin receptor and, therefore, are useful as melatonergic agents.

10 Claims, No Drawings

BENZOXAZOLE DERIVATIVES AS NOVEL MELATONERGIC AGENTS

This application claims benefit of provisional appln. No. 60/363,817 filed Mar. 12, 2002.

BACKGROUND OF THE INVENTION

The invention pertains to novel benzoxazole derivatives having drug and bio-affecting properties, to their preparation, to pharmaceutical formulations containing them and to methods of using them. These compounds possess melatonergic properties that should make them useful in treating certain medical disorders.

Melatonin (N-acetyl-5-methoxytryptamine) is a hormone which is synthesized and secreted primarily by the pineal gland. In mammals, melatonin levels show a cyclical, circadian pattern, with highest levels occurring during the dark period of a circadian light-dark cycle. Melatonin is involved in the transduction of photoperiodic information and appears to modulate a variety of neural and endocrine functions in vertebrates, including the regulation of reproduction, body weight and metabolism in photoperiodic mammals, the control of circadian rhythms and the modulation of retinal physiology.

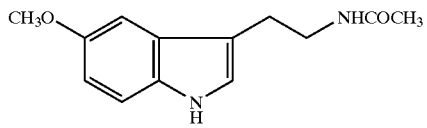

Recent evidence demonstrates that melatonin exerts its biological effects through specific receptors. Use of the biologically active, radiolabelled agonist [$^{125}$I]-2-iodomelatonin has led to the identification of high affinity melatonin receptors in the central nervous systems (CNS) of a variety of species. The sequence of one such high affinity melatonin receptor, cloned from frog melanocytes, has been reported. In the mammalian brain, autoradiographic studies have localized the distribution of melatonin receptors to a few specific structures.

Although there are significant differences in melatonin receptor distribution even between closely related species, in general the highest binding site density occurs in discrete nuclei of the hypothalamus. In humans, specific [$^{125}$I]-2-iodomelatonin binding within the hypothalamus is completely localized to the suprachiasmatic nucleus, strongly suggesting that melatonin receptors are located within the human biological clock.

Exogenous melatonin administration has been found to synchronize circadian rhythms in rats (Cassone, et al., *J. Biol. Rythms*, 1:219–229, 1986). In humans, administration of melatonin has been used to treat jet-lag related sleep disturbances, considered to be caused by desynchronization of circadian rhythms (Arendt, et al., *Br. Med. J.* 292:1170, 1986). Further, the use of a single dose of melatonin to induce sleep in humans has been claimed by Wurtman in International Patent Application WO 94/07487 published on Apr. 14, 1994.

Melatonin binding sites have been found in diverse tissues of the body—i.e., in the retina, superchiasmatic nucleus, spleen, etc. This means that melatonin exerts multiple physiological effects and is not highly selective. The potential for side effects with melatonin use is large. Melatonin agonists should be more selective than melatonin and have fewer side effects. Suitable melatonin agonists could overcome melatonin's drawbacks, resulting in products having more predictable and, possibly, sustained activity.

Melatonin agonists should be particularly useful for the treatment of chronobiological disorders. They would also be useful for the further study of melatonin receptor interactions as well as in the treatment of conditions affected by melatonin activity, such as depression, work-shift syndrome, sleep disorders, glaucoma, reproduction, cancer, periondontitis, immune disorders, neuroendocrine disorders, and a variety of sleep disorders.

Aside from simple indole derivatives of melatonin itself, various amide structures have been prepared and their use as melatonin ligands disclosed. In general these amide structures can be represented as:

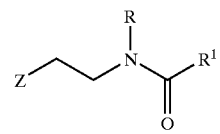

wherein Z is an aryl or heteroaryl system attached by a two carbon chain to the amide group. Some specific examples follow.

Yous, et al. in European Patent Application No. EP 527 687 A disclose, as melatonin ligands, ethylamines having cyclic substituents:

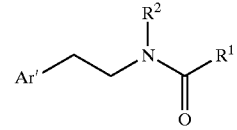

wherein Ar' is, inter alia, a substituted or unsubstituted benzo[b]thiophen-3-yl, benzimidazol-1-yl, benzo[b]furan-3-yl, 1,2-benzisoxazol-3-yl, 1,2-benzisothiazol-3-yl, or indazol-3-yl radical; $R_1$ is, inter alia, an alkyl or cycloalkyl group; and $R_2$ is hydrogen or lower alkyl.

Matsuda, et al. in International Patent Application No. WO 95/22521 disclose 1-phenyl-2-(1-aminoalkyl)-N,N-diethylcyclopropanecarboxamides as N-methyl-D-aspartate (NMDA) receptor antagonists, wherein $R_1$ represents, inter alia, a $C_1$–$C_5$ linear saturated aliphatic, a $C_1$–$C_5$ linear unsaturated aliphatic, a branched aliphatic, or a phenyl group which may be substituted with one to three substituents selected independently from the group consisting of halogen, $C_1$–$C_4$ alkyl, nitro, amino, hydroxy, and $C_1$–$C_4$ alkoxy as shown below:

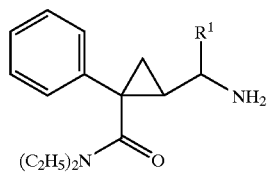

The 1,2-diarylcyclopropane derivatives disclosed in NE 6701256 have CNS stimulant properties:

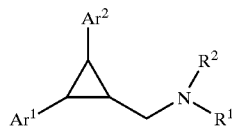

wherein Ar$_1$ and Ar$_2$ are independently and optionally substituted phenyl; R$_1$ is inter alia hydrogen, lower alkyl or acyl; R$_2$ is inter alia alkyl, cycloalkyl or aralkyl.

Keavy et al. In U.S. Pat. No. 5,753,709 issued on May 19, 1998, and assigned to the assignee of the present invention, discloses melatonergic agents of the following structure:

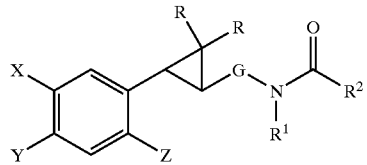

wherein X represents halogen, hydrogen, cyano, aryl, C$_{1-4}$ alkyl or OR$^5$ wherein, inter alia, R$^5$ is hydrogen, C$_{1-20}$ alkyl or C$_{4-20}$ alkylcycloalkyl; Y is hydrogen or halogen; R is hydrogen, halogen or C$_{1-4}$ alkyl; R$^1$ is hydrogen, C$_{1-4}$ alkyl or benzyl; and R$^2$ is C$_{1-6}$ alkyl, C$_{2-6}$ alkenyl, C$_{3-6}$ cycloalkyl, C$_{2-4}$ alkoxyalkyl, C$_{1-4}$ trifluoromethylalkyl or C$_{2-8}$ alkylthioalkyl.

Catt et al. in U.S. Pat. No. 5,856,529 issued on Jan. 5, 1999, and assigned to the assignee of the present invention, discloses melatonergic agents of the following structure:

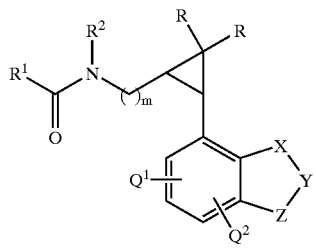

wherein Q$^1$ and Q$^2$ represent hydrogen or halogen; X is CH$_2$, CH or oxygen; Y is CR$^3$, C$^3$R$^4$ or (CH$_2$)$_n$ whereby n is 1 to 4; Z is CH$_2$, CH or oxygen; R is hydrogen, halogen or C$_{1-4}$ alkyl; m is 1 or 2; R$^2$ is hydrogen or C$_{1-4}$ alkyl; and R$^1$ is C$_{1-6}$ alkyl, C$_{3-6}$ cycloalkyl, C$_{1-3}$ haloalkyl, C$_{1-6}$ alkylamino, C$_{2-6}$ alkenyl, C$_{1-4}$ alkoxy(C$_{1-4}$)alkyl, C$_{1-4}$ alkylthio(C$_{1-4}$)alkyl or C$_{1-4}$ trifluoromethylalkyl.

Takaki et al. in U.S. Pat. No. 6,211,225 issued on Apr. 3, 2001, and assigned to the assignee of the present invention, discloses melatonergic agents of the following structure:

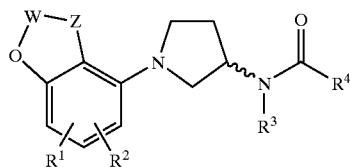

wherein the wavy bond ~~~ represents the racemate, the (R)-enantiomer or the (S)-enantiomer; R$^1$ and R$^2$ each are independently hydrogen or halogen; W is CR$^5$, CR$^5$R$^6$ or (CH$_2$)$_n$ with n being 1 to 2; Z is CH$_2$, CH or oxygen; R$^3$ is hydrogen or C$_{1-4}$ alkyl; R$^4$ is C$_{1-6}$ alkyl, C$_{3-6}$ cycloalkyl, C$_{1-3}$ haloalkyl, C$_{1-6}$ alkylamino, C$_{2-6}$ alkenyl, C$_{1-4}$ alkoxy (C$_{1-4}$)alkyl, C$_{1-4}$ alkylthio(C$_{1-4}$)alkyl or C$_{1-4}$ trifluoromethylalkyl; R$^5$ and R$^6$ are each independently hydrogen or C$_{1-4}$ alkyl.

The foregoing disclosures do not teach or suggest the novel melatonergic benzoxazole derivatives of the present invention. The novel compounds of the present invention display melatonergic agonist activity.

SUMMARY OF THE INVENTION

The present invention is directed to, in a first aspect, a compound of Formula I:

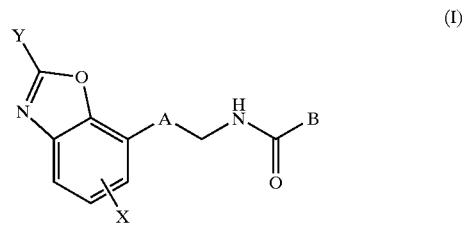

(I)

or a pharmaceutically acceptable salt or solvate thereof wherein

A is C$_{1-4}$ alkylene or 1,2 disubstituted cyclopropyl;

B is C$_{1-6}$ alkyl, C$_{3-6}$ cycloalkyl, C$_{1-6}$ alkoxy, or C$_{1-4}$ alkylamino;

X is hydrogen, halogen, C$_{2-4}$ alkenyl, C$_{1-6}$ alkyl, furyl, or phenyl optionally substituted with halogen, C$_{1-6}$ alkoxy, or haloalkyl; and Y is hydrogen, phenyl, or C$_{1-6}$ alkyl optionally substituted with phenyl.

In another aspect, the present invention is directed to a method of treating a circadian rhythm-related disorder in a mammal in need of such treatment comprising administering to the mammal a therapeutically effective amount of a compound of Formula I.

In yet another aspect, the present invention is directed to a pharmaceutical composition for treating circadian rhythm-related disorders comprising a therapeutically effective amount of a compound as defined by Formula I and a pharmaceutically acceptable carrier, adjuvant or diluent.

DETAILED DESCRIPTION OF THE INVENTION

The present invention provides a novel series of compounds of Formula I and hydrates thereof:

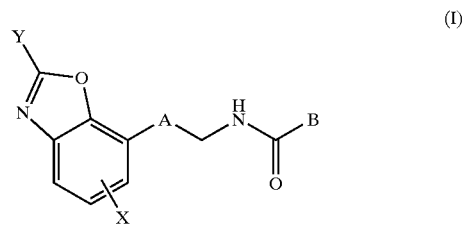

(I)

or a pharmaceutically acceptable salt or solvate thereof wherein

A is C$_{1-4}$ alkylene or 1,2 disubstituted cyclopropyl;

B is C$_{1-6}$ alkyl, C$_{3-6}$ cycloalkyl, C$_{1-6}$ alkoxy, or C$_{1-4}$ alkylamino;

X is hydrogen, halogen, $C_{2-4}$ alkenyl, $C_{1-6}$ alkyl, furyl, or phenyl optionally substituted with halogen, $C_{1-6}$ alkoxy, or haloalkyl; and Y is hydrogen, phenyl, or $C_{1-6}$ alkyl optionally substituted with phenyl.

"Alkenyl" means a straight or branched hydrocarbon radical containing a carbon-carbon double bond such as vinyl, propenyl, and butenyl.

"Alkyl" means a straight or branched chain group such as methyl, ethyl, propyl, isopropyl, butyl, t-butyl, pentyl, hexyl, and the like.

"Alkylene" means a divalent alkyl radical such as methylene, ethylene, propylene, butylene, and the like.

"Alkoxy" refers to monovalent substituents of the structure: —O-alkyl, wherein alkyl is as defined above.

"Cycloalkyl" groups are cyclic alkyl moieties as used herein and in the claims to include such groups as cyclopropyl, cyclobutyl, cyclopentyl, and cyclohexyl. The cyclopropyl group is a preferred cycloalkyl moiety.

"Halogen" means fluorine, chlorine, bromine, or iodine. Preferred halogens in haloalkyl moieties are fluorine and chlorine.

"Haloalkyl" includes straight and branched chain hydrocarbon radicals bearing from 1 to 3 halogen moieties.

The term "pharmaceutically acceptable salt" as used herein and in the claims is intended to include nontoxic inorganic acids such as hydrochloric, hydrobromic, hydroiodic, sulfuric, nitric, phosphoric and the like, and nontoxic organic acids such as acetic, benzoic, fumaric, cinnamic, mandelic, succinic, citric, maleic, lactic and the like.

The term "hydrate or solvate thereof" as used herein and in the claims is intended to include hydrated forms such as monohydrate, dihydrate, hemihydrate, sesquihydrate, trihydrate, tetrahydrate and the like as well as solvated forms. The products may be true hydrates, while in other cases, the products may merely retain adventitious water or be a mixture of water plus some adventitious solvent. It should be appreciated by those skilled in the art that hydrated and/or solvated forms are equivalent to unsolvated forms and are intended to be encompassed within the scope of the present invention.

The compounds of Formula I encompass all pharmaceutically acceptable solvates, particularly hydrates, thereof. The present invention also encompasses diastereomers as well as optical isomers, e.g., mixtures of enantiomers including racemic mixtures, as well as individual enantiomers and diastereomers, which arise as a consequence of structural asymmetry in certain compounds of Formula I. Separation of individual isomers or selective synthesis of the individual isomers is accomplished by application of various methods known to those of skill in the art.

Preferred compounds of the present invention may be further defined by the structure of Formula II:

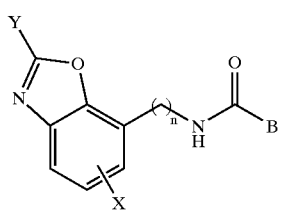

(II)

wherein n is 2 to 4, preferably n is 3;

B is $C_{1-3}$ alkyl, $C_3$ cycloalkyl, $C_{1-4}$ alkoxy, or $C_{1-4}$ alkylamino;

X is hydrogen, halogen, $C_{2-4}$ alkenyl, $C_{1-2}$ alkyl, furyl, or phenyl optionally substituted with halogen, $C_{1-2}$ alkoxy, or haloalkyl; and Y is hydrogen, phenyl, or $C_{1-4}$ alkyl group optionally substituted with phenyl.

The compounds of Formula II may be synthesized according to the following reaction schemes.

Reaction Scheme 1

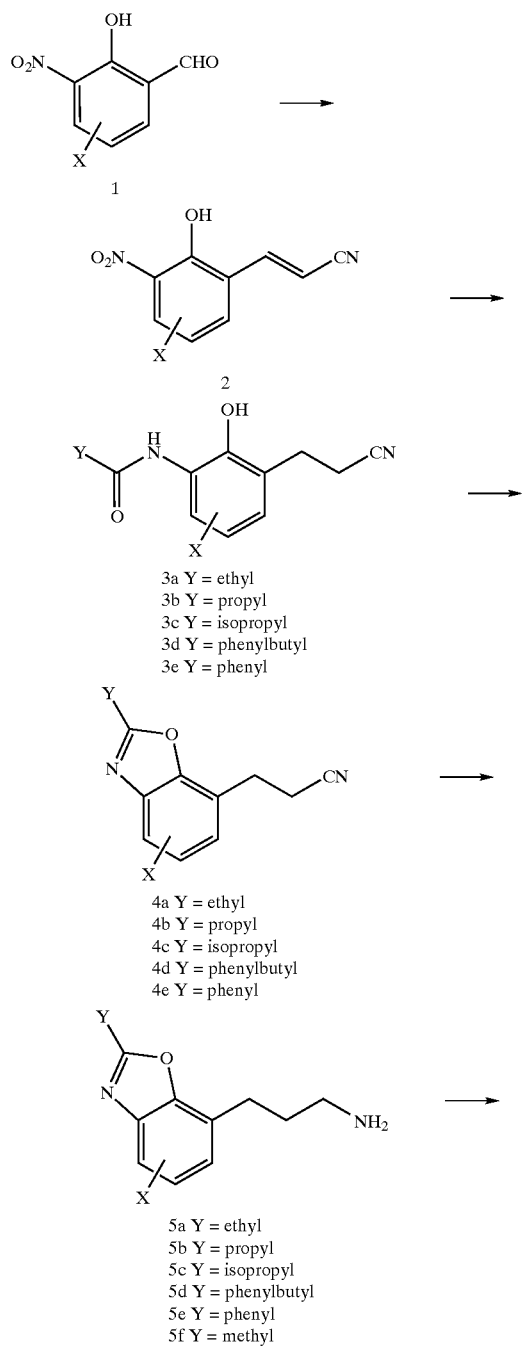

-continued

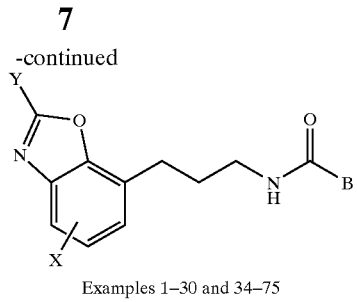

Examples 1–30 and 34–75

Wherein Y is a methyl group, Reaction Scheme 1A illustrates a more precise route to the final product, particularly in Examples 1 to 6.

Reaction Scheme 1A:

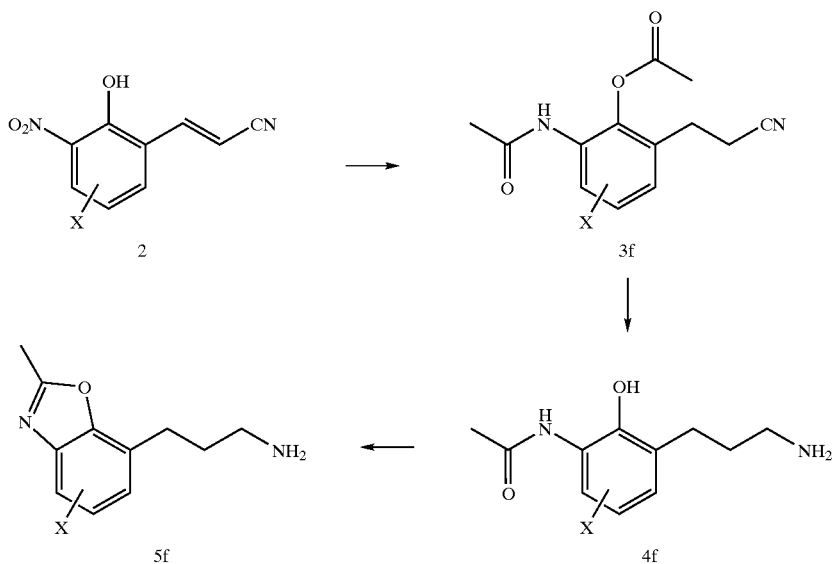

In Reaction Scheme 1, the commercially available benzaldehyde 1 was homolygated with diethylcyanomethylphosphonate in a Horner-Emmons reaction. The resulting cinnamonitrile 2 was hydrogenated in the presence of the appropriate anhydride or acid chloride. Quenching this reaction mixture with aqueous sodium hydroxide selectively saponified the ester producing amides 3a to 3e. Heating these amides in the presence of pyridinium p-tolylsulfonate produced the benzoxazoles 4a to 4e. Hydrogenation of these nitrites with Raney nickel followed by acylation afforded examples 1 to 30 and 34 to 75.

In order to synthesize Examples 1 to 6, the commercially available benzaldehyde 1 was homolygated with diethylcyanomethylphosphonate in a Horner-Emmons reaction. The resulting cinnamonitrile 2 was hydrogenated with Raney Nickel which selectively saponified the ester in addition to reducing the nitrile. Heating the amine 4f in the presence of pyridinium p-tolylsulfonate produced the benzoxazole 5f which were later acylated to give the resultant benzoxazoles wherein Y is methyl.

Some preferred compounds prepared by Reaction Scheme 1 are

N-[3-(2-methylbenzoxazol-7-yl)propyl]propanamide;
N-[3-(2-methylbenzoxazol-7-yl)propyl]butanamide;
cyclopropyl-N-[3-(2-methylbenzoxazol-7-yl)propyl]carboxamide;
2-methyl-N-[3-(2-methylbenzoxazol-7-yl)propyl]propanamide;
N-[3-(2-ethylbenzoxazol-7-yl)propyl]propanamide;
N-[3-(2-ethylbenzoxazol-7-yl)propyl]butanamide;
cyclopropyl-N-[3-(2-ethylbenzoxazol-7-yl)propyl]carboxamide;
N-{3-[2-(4-phenylbutyl)benzoxazol-7-yl]propyl}acetamide;
N-{3-[2-(4-phenylbutyl)benzoxazol-7-yl]propyl}propanamide;
N-{3-[2-(4-phenylbutyl)benzoxazol-7-yl]propyl}butanamide;
2-methyl-N-{3-[2-(4-phenylbutyl)benzoxazol-7-yl]propyl}propanamide;
cyclopropyl-N-{3-[2-(4-phenylbutyl)benzoxazol-7-yl]propyl}carboxamide;
(ethylamino)-N-{3-[2-(4-phenylbutyl)benzoxazol-7-yl]propyl}carboxamide;
and N-(3-benzoxazol-7-ylpropyl)-2-methylpropanamide.

Some preferred compounds where there is X substitution on the benzoxazole ring include:

N-[3-(6-bromo-2-ethylbenzoxazol-7-yl)propyl]acetamide;
N-[3-(2-ethyl-6-vinylbenzoxazol-7-yl)propyl]acetamide;
cyclopropyl-N-[3-(2-ethyl-6-methylbenzoxazol-7-yl)propyl]carboxamide;
cyclopropyl-N-{3-[2-ethyl-6-(4-fluorophenyl)benzoxazol-7-yl]propyl}carboxamide;
N-{3-[2-ethyl-6-(4-methoxyphenyl)benzoxazol-7-yl]propyl}acetamide;
N-[3-(2-ethyl-6-phenylbenzoxazol-7-yl)propyl]acetamide;
cyclopropyl-N-[3-(2-ethyl-6-phenylbenzoxazol-7-yl)propyl]carboxamide;
N-[3-(2-ethyl-6-(2-furyl)benzoxazol-7-yl)propyl]acetamide; and
cyclopropyl-N-[3-(2-ethyl-6-(2-furyl)benzoxazol-7-yl)propyl]carboxamide.

When Y is hydrogen, the compounds may be synthesized in accordance with the following Reaction Scheme 2.

Reaction Scheme 2:

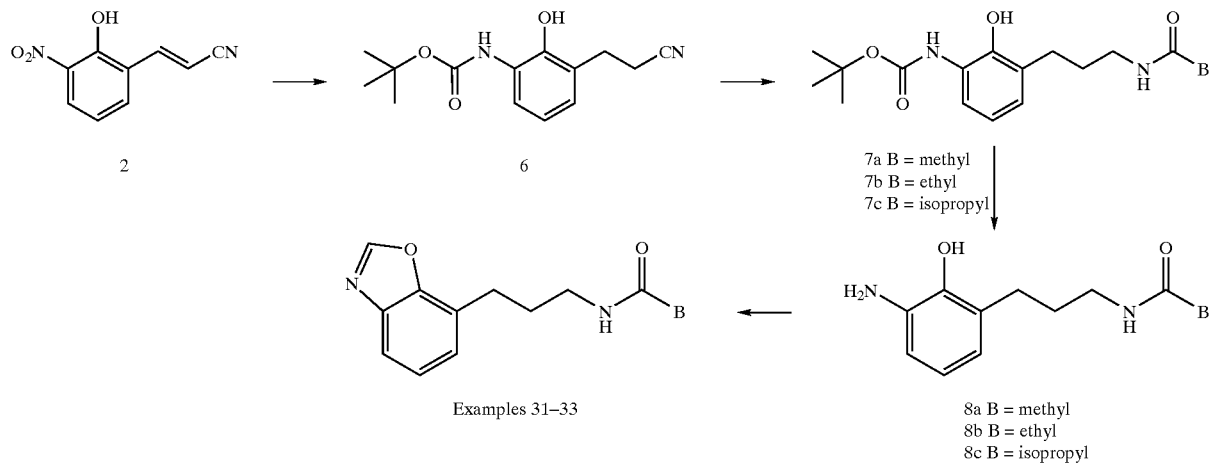

Cinnamonitrile 2 was hydrogenated over 10% palladium on carbon in the presence of di-t-butyldicarbonate to give nitrile 6. Further hydrogenation with Raney nickel in the presence of the appropriate anhydride yielded compounds 7a to 7c. Deprotection of the BOC group with hydrochloric acid followed by cyclization with ethyl orthoformate produced examples 31 to 33.

Preferred compounds of the present invention include those of Formula I wherein A is a 1,2 disubstituted cyclopropyl as represented by Formula III:

(III)

wherein

B is $C_{1-6}$ alkyl group or $C_3$ cycloalkyl group, or $C_{1-4}$ alkylamino;

X is hydrogen, halogen, $C_{2-4}$ alkenyl, $C_{1-2}$ alkyl, furyl, or phenyl optionally substituted with halogen, $C_{1-2}$ alkoxy, or haloalkyl; and Y is hydrogen, phenyl, or $C_{1-4}$ alkyl group optionally substituted with phenyl.

A more preferred group of compounds comprises X is hydrogen. The trans configuration of the compounds of Formula III is more preferred.

The compounds of Formula III may be synthesized in accordance with Reaction Scheme 3.

Reaction Scheme 3

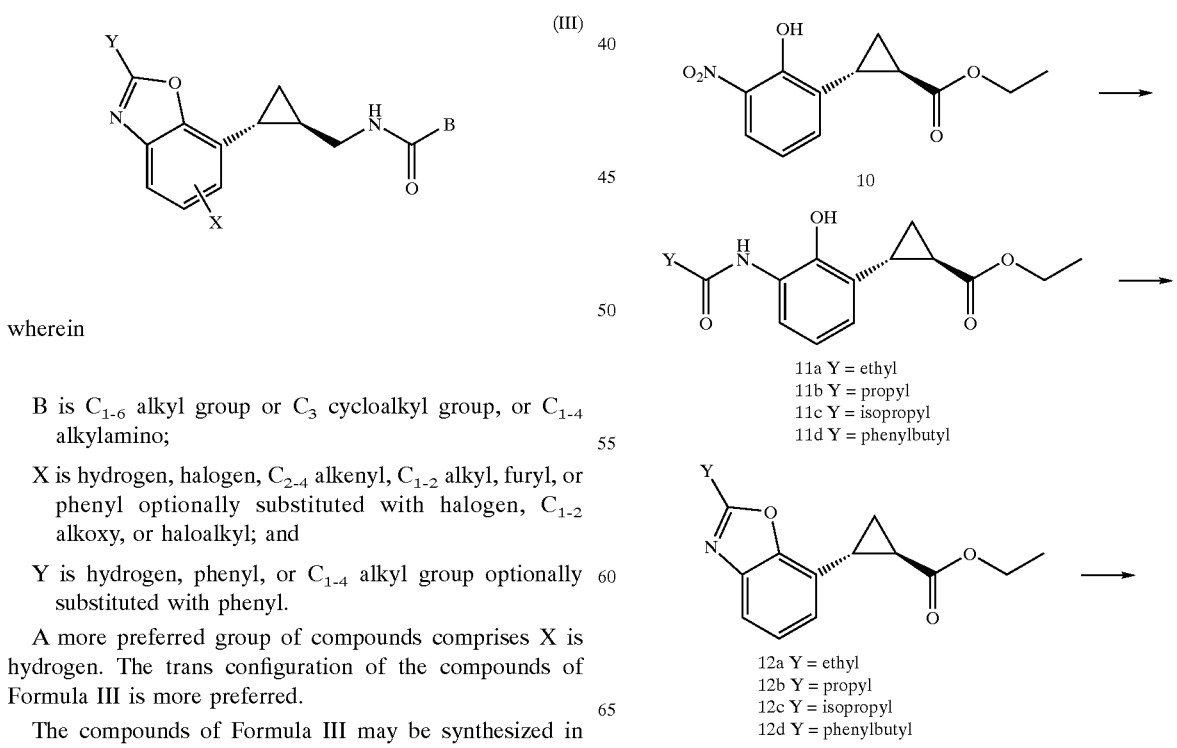

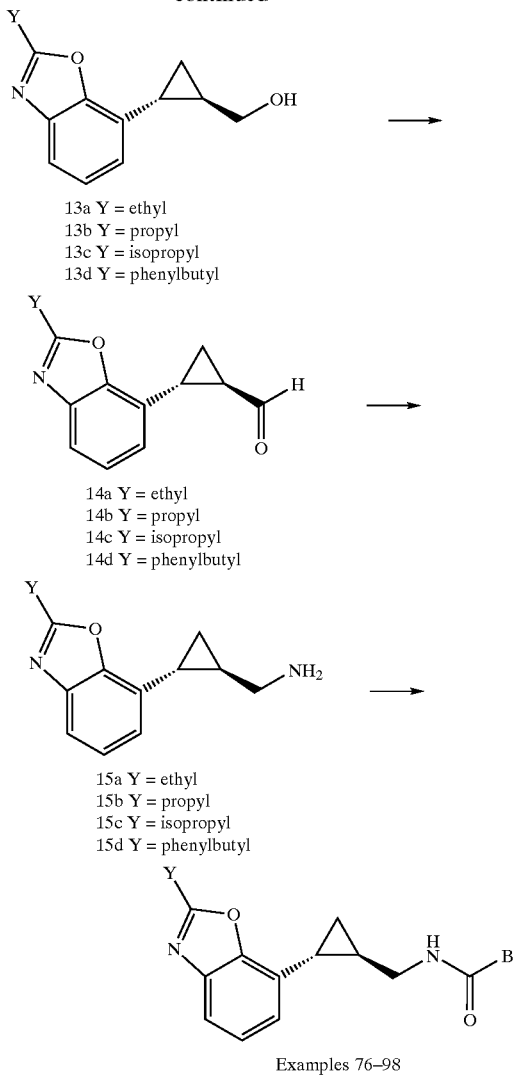

13a Y = ethyl
13b Y = propyl
13c Y = isopropyl
13d Y = phenylbutyl

14a Y = ethyl
14b Y = propyl
14c Y = isopropyl
14d Y = phenylbutyl

15a Y = ethyl
15b Y = propyl
15c Y = isopropyl
15d Y = phenylbutyl

Examples 76–98

Nitrosalicyaldehyde was homolygated by a Wittig reaction to give the cinnamate 9. Cyclopropanation to intermediate 10 was accomplished with diazomethane and palladium catalyzation. The nitro group was reduced and acetylated by hydrogenation in the presence of the appropriate anhydride or acid chloride to intermediates 11a to 11d. Cyclization to the benzoxazole 12a to 12d was accomplished by heating in the presence of pyridinium p-tolylsulfonate. The ester 12a to 12d was converted to the aldehyde 14a to 14d by reduction to the alcohol 13a to 13d followed by oxidation. Reduction of the oxime followed by acylation produced Examples 76 to 98.

Some preferred compounds of Formula III include:

N-{[(1R,2R)-2-(2-ethylbenzoxazol-7-yl)cyclopropyl]methyl}acetamide;
N-{[(1R,2R)-2-(2-ethylbenzoxazol-7-yl)cyclopropyl]methyl}propanamide;
N-{[(1R,2R)-2-(2-ethylbenzoxazol-7-yl)cyclopropyl]methyl}butanamide;
N-{[(1R,2R)-2-(2-ethylbenzoxazol-7-yl)cyclopropyl]methyl}-2-methylpropanamide;
N-{[(1R,2R)-2-(2-ethylbenzoxazol-7-yl)cyclopropyl]methyl}cyclopropylcarboxamide;
N-{[(1R,2R)-2-(2-ethylbenzoxazol-7-yl)cyclopropyl]methyl}(ethylamino)carboxamide;
N-{[(1R,2R)-2-(2-propylbenzoxazol-7-yl)cyclopropyl]methyl}acetamide;
N-({(1R,2R)-2-[2-(methylethyl)benzoxazol-7-yl]cyclopropyl}methyl)acetamide; N-{[(1R,2R)-2-(2-propylbenzoxazol-7-yl)cyclopropyl]methyl}propanamide;
N-({(1R,2R)-2-[2-(methylethyl)benzoxazol-7-yl]cyclopropyl}methyl)propanamide;
N-{[(1R,2R)-2-(2-propylbenzoxazol-7-yl)cyclopropyl]methyl}butanamide;
N-({(1R,2R)-2-[2-(methylethyl)benzoxazol-7-yl]cyclopropyl}methyl)butanamide;
N-{[(1R,2R)-2-(2-propylbenzoxazol-7-yl)cyclopropyl]methyl}-3-methylbutanamide;
N-({(1R,2R)-2-[2-(methylethyl)benzoxazol-7-yl]cyclopropyl}methyl)-3-methylbutanamide;
N-{[(1R,2R)-2-(2-propylbenzoxazol-7-yl)cyclopropyl]methyl}cyclopropylcarboxamide;
N-({(1R,2R)-2-[2-(methylethyl)benzoxazol-7-yl]cyclopropyl}methyl)cyclopropylcarboxamide;
N-{[(1R,2R)-2-(2-propylbenzoxazol-7-yl)cyclopropyl]methyl}(ethylamino)carboxamide;
N-({(1R,2R)-2-[2-(methylethyl)benzoxazol-7-yl]cyclopropyl}methyl)(ethylamino)carboxamide;
N-({(1R,2R)-2-[2-(4-phenylbutyl)benzoxazol-7-yl]cyclopropyl}methyl)acetamide;
N-({(1R,2R)-2-[2-(4-phenylbutyl)benzoxazol-7-yl]cyclopropyl}methyl)propanamide;
N-({(1R,2R)-2-[2-(4-phenylbutyl)benzoxazol-7-yl]cyclopropyl}methyl)butanamide;
N-({(1R,2R)-2-[2-(4-phenylbutyl)benzoxazol-7-yl]cyclopropyl}methyl)-2-methylpropanamide; and
N-({(1R,2R)-2-[2-(4-phenylbutyl)benzoxazol-7-yl]cyclopropyl}methyl)cyclopropylcarboxamide.

Biological Data:

The compounds of the present invention are melatonergic agents. They have been found to bind to human melatonergic receptors expressed in a stable cell line with good affinity. Further, the compounds are agonists as determined by their ability, like melatonin, to block the forskolin-stimulated accumulation of cAMP in certain cells. Due to these properties, the compounds and compositions of the present invention should be useful as sedatives, chronobiotic agents, anxiolytics, antipsychotics, analgesics, and the like. Specifically, these agents should find use in the treatment of stress, sleep disorders, seasonal depression, appetite regulation, shifts in circadian cycles, melancholia, benign prostate hyperplasia, inflammatory articular disease, periodontitis, and related conditions.

Melatonergic Receptor Binding Activity

1. Reagents:
   (a) TME=50 mM Tris buffer containing 12.5 mM $MgCl_2$, and 2 mM EDTA, pH 7.4 at 37° C., with concentrated HCl.
   (b) Wash buffer: 20 mM Tris base containing 2 mM $MgCl_2$, pH 7.4 at room temperature.
   (c) $10^{-4}$ M melatonin ($10^{-5}$ M final concentration).
   (d) 2-[$^{125}$I]-iodomelatonin $ML_{1a}$, 0.1 nM final concentration.
   (e) 2-[$^{125}$I]-iodomelatonin $ML_{1b}$, 0.2 nM final concentration.

2. Membrane Homogenates: The melatonin $ML_{1a}$ and $ML_{1b}$ receptors cDNA were individually subcloned into pcDNA3 and introduced into NIH-3T3 cells using Lipofectamine. Transformed NIH-3T3 cells resistant to geneticin (G-418) were isolated, and single colonies expressing high levels of 2[$^{125}$I]-iodomelatonin binding were isolated. Cells are maintained in DMEM supplemented with 10% calf serum and G-418 (0.5 g/liter). Cells are grown to confluency in T-175 flasks, scraped using Hank's balanced salt solution, and frozen at −80° C. For preparing membrane homogenates, pellets are thawed on ice, and re-suspended in TME buffer in the presence of 10 μg/ml aprotinin and leupeptin, and 100 μM phenylmethylsulfonylfluoride. The cells were then homogenized using a dounce homogenizer, and centrifuged. The resulting pellet was re-suspended with dounce homogenizer in TME (supplemented with the above protease inhibitors) and frozen. On the day of assay, a small aliquot was thawed on ice and re-suspended in the ice cold TME (1:50–1:100 v/v) and held on ice until assayed.

3. Incubation: 37° C. for 1 hour. Reaction is terminated by filtration. Filters were washed 3 times.

4. References: Reppert, S. M. et al., *Neuron*, 13, p. 1177–1185 (1994); and Reppert, S. M. et al., *Proc. Natl. Acad. Sci. USA*, 92, p. 8734–8738 (1995).

Based on biological tests, the following Formula I compounds are preferred. Those with binding affinities for the human melatonin receptor with $IC_{50}$ of 250 nM or less are most preferred. All Formula I compounds are shown in Tables I to III.

TABLE I

| Ex. | B | Y | $ML_{1a}$ ($IC_{50}$, nM) | $ML_{1b}$ ($IC_{50}$, nM) |
|---|---|---|---|---|
| 1 | methyl | methyl | ++ | ++ |
| 2 | ethyl | methyl | +++ | +++ |
| 3 | propyl | methyl | +++ | +++ |
| 4 | cyclopropyl | methyl | +++ | +++ |
| 5 | isopropyl | methyl | +++ | +++ |
| 6 | ethylamino | methyl | ++ | ++ |
| 7 | methyl | ethyl | ++ | +++ |
| 8 | ethyl | ethyl | +++ | +++ |
| 9 | propyl | ethyl | ++ | +++ |
| 10 | isopropyl | ethyl | ++ | ++ |
| 11 | cyclopropyl | ethyl | +++ | ++ |
| 12 | ethylamino | ethyl | ++ | ++ |
| 13 | methyl | propyl | + | ++ |
| 14 | ethyl | propyl | ++ | ++ |
| 15 | propyl | propyl | + | ++ |
| 16 | isopropyl | propyl | ++ | ++ |
| 17 | cyclopropyl | propyl | ++ | ++ |
| 18 | ethylamino | propyl | + | ++ |
| 19 | methyl | phenyl | ++ | ++ |
| 20 | ethyl | phenyl | ++ | ++ |
| 21 | propyl | phenyl | ++ | ++ |
| 22 | isopropyl | phenyl | ++ | ++ |
| 23 | cyclopropyl | phenyl | ++ | ++ |
| 24 | ethylamino | phenyl | + | ++ |
| 25 | methyl | phenylbutyl | +++ | ++ |
| 26 | ethyl | phenylbutyl | +++ | ++ |
| 27 | propyl | phenylbutyl | +++ | ++ |
| 28 | isopropyl | phenylbutyl | +++ | ++ |
| 29 | cyclopropyl | phenylbutyl | +++ | ++ |
| 30 | ethylamino | phenylbutyl | +++ | ++ |
| 31 | methyl | hydrogen | ++ | ++ |
| 32 | ethyl | hydrogen | ++ | +++ |
| 33 | isopropyl | hydrogen | ++ | +++ |
| 34 | methyl | isopropyl | ++ | ++ |
| 35 | ethyl | isopropyl | ++ | ++ |
| 36 | propyl | isopropyl | ++ | ++ |
| 37 | isopropyl | isopropyl | ++ | ++ |
| 38 | cyclopropyl | isopropyl | ++ | + |
| 39 | ethylamino | isopropyl | + | ++ |

+++ = <10 nM;
++ = 10–250 nM;
+ = >250 nM

TABLE II

| Ex. | B | X | $ML_{1a}$ ($IC_{50}$, nM) | $ML_{1b}$ ($IC_{50}$, nM) |
|---|---|---|---|---|
| 40 | trimethylmethoxy | bromo | ++ | + |
| 41 | trimethylmethoxy | vinyl | + | + |
| 42 | methyl | bromo | ++ | +++ |
| 43 | methyl | vinyl | ++ | +++ |
| 44 | methyl | methyl | ++ | ++ |
| 45 | phenyl | methyl | ++ | ++ |
| 46 | cyclopropyl | methyl | +++ | +++ |
| 47 | methyl | fluorophenyl | ++ | +++ |
| 48 | phenyl | fluorophenyl | + | ++ |
| 49 | cyclopropyl | fluorophenyl | ++ | +++ |
| 50 | methyl | trifluorobenzyl | + | ++ |
| 51 | cyclopropyl | trifluorobenzyl | + | ++ |
| 52 | methyl | methoxyphenyl | ++ | +++ |
| 53 | phenyl | methoxyphenyl | + | + |
| 54 | cyclopropyl | methoxyphenyl | + | ++ |
| 55 | methyl | phenyl | +++ | +++ |
| 56 | phenyl | phenyl | ++ | ++ |
| 57 | cyclopropyl | phenyl | ++ | +++ |
| 58 | methyl | fluorophenyl | ++ | ++ |
| 59 | phenyl | fluorophenyl | + | + |
| 60 | cyclopropyl | fluorophenyl | ++ | ++ |
| 61 | phenyl | trifluorobenzyl | ++ | + |
| 62 | methyl | methoxyphenyl | ++ | ++ |
| 63 | phenyl | methoxyphenyl | ++ | + |
| 64 | cyclopropyl | methoxyphenyl | + | + |
| 65 | methyl | phenyl | + | ++ |
| 66 | phenyl | phenyl | + | + |
| 67 | cyclopropyl | phenyl | ++ | + |
| 68 | methyl | bromo | + | ++ |
| 69 | phenyl | bromo | + | + |
| 70 | cyclopropyl | bromo | + | ++ |
| 71 | phenyl | vinyl | + | + |
| 72 | cyclopropyl | vinyl | + | + |
| 73 | methyl | furyl | +++ | +++ |
| 74 | phenyl | furyl | + | + |
| 75 | cyclopropyl | furyl | ++ | +++ |

+++ = <10 nM;
++ = 10–250 nM;
+ = >250 nM

TABLE III

| Ex. | B | Y | ML$_{1a}$ (IC$_{50}$, nM) | ML$_{1b}$ (IC$_{50}$, nM) |
|---|---|---|---|---|
| 76 | methyl | ethyl | +++ | +++ |
| 77 | ethyl | ethyl | +++ | +++ |
| 78 | propyl | ethyl | +++ | +++ |
| 79 | isopropyl | ethyl | +++ | +++ |
| 80 | cyclopropyl | ethyl | +++ | +++ |
| 81 | ethylamino | ethyl | +++ | +++ |
| 82 | methyl | propyl | +++ | +++ |
| 83 | methyl | isopropyl | ++ | +++ |
| 84 | ethyl | propyl | +++ | +++ |
| 85 | ethyl | isopropyl | +++ | +++ |
| 86 | propyl | propyl | +++ | +++ |
| 87 | propyl | isopropyl | +++ | +++ |
| 88 | isopropyl | propyl | +++ | +++ |
| 89 | isopropyl | isopropyl | +++ | +++ |
| 90 | cyclopropyl | propyl | +++ | +++ |
| 91 | cyclopropyl | isopropyl | +++ | +++ |
| 92 | ethylamino | propyl | +++ | +++ |
| 93 | ethylamino | isopropyl | ++ | ++ |
| 94 | methyl | phenylbutyl | +++ | +++ |
| 95 | ethyl | phenylbutyl | +++ | +++ |
| 96 | propyl | phenylbutyl | +++ | +++ |
| 97 | isopropyl | phenylbutyl | +++ | +++ |
| 98 | cyclopropyl | phenylbutyl | +++ | +++ |

+++ = <10 nM;
++ = 10–250 nM;
+ = >250 nM

The compounds of the present invention have affinity for receptors of the endogenous pineal hormone, melatonin, as determined in receptor binding assays described above in Tables I to III for the ML$_{1a}$ and ML$_{1b}$ (human) receptors. Melatonin is involved in the regulation of a variety of biological rhythms and exerts its biological effects via interaction with specific receptors. There is evidence that administration of melatonin agonists are of clinical utility in the treatment of various conditions regulated by melatonin activity. Such conditions include depression, jet-lag, work-shift syndrome, sleep disorders, glaucoma, some disorders associated with reproduction, cancer benign prostatic hyperplasia, immune disorders, and neuroendocrine disorders.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally with pharmaceutically acceptable adjuvants and excipients employing standard conventional techniques.

The pharmaceutical compositions include suitable dosage forms for oral, parenteral (including subcutaneous, intramuscular, intradermal and intravenous) transdermal, bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and the like may be utilized. Injectable suspensions also may be used, in which case conventional suspending agents may be employed. Conventional preservatives, buffering agents and the like also may be added to the parenteral dosage forms. Particularly useful is the administration of a compound of Formula I in oral dosage formulations. The pharmaceutical compositions are prepared by conventional techniques appropriate to the desired preparation containing appropriate amounts of the active ingredient, that is, the compound of Formula I according to the invention. See for example, *Remington's Pharmaceutical Sciences*, Mack Publishing Company, Easton, Pa., 17$^{th}$ edition, 1985.

In making pharmaceutical compositions containing compounds of the present invention, the active ingredient(s) will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or a liquid medium), ointments containing for example up to 10% by weight of the active compound, soft and hard gelatin capsules, suppositories, sterile injectable solutions, and sterile packaged powders.

Some examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate and mineral oil. The formulations can additionally include lubricating agents, wetting agents emulsifying and suspending agents, preserving agents, sweetening agents or flavoring agents. The compositions of the invention may be formulated so as to provide quick, sustained or delayed release of the active ingredient after administration to the patient.

The dosage of the compounds of Formula I to achieve a therapeutic effect will depend not only on such factors as the age, weight and sex of the patient, and mode of administration, but also on the degree of melatonergic activity desired and the potency of the particular compound being utilized for the particular disorder or condition concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

The compositions are preferably formulated in a unit dosage form, each dosage containing from about 0.1 to 100 mg, more usually 1 to 10 mg, of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

These active compounds are effective over a wide dosage range. For example, dosages per day will normally fall within the range of about 0.1 to 500 mg. In the treatment of adult humans, the range of about 0.1 to 10 mg/day, in single or divided doses, is preferred. Generally, the compounds of the invention may be used in treating sleep and related disorders in a manner similar to that used in treating sleep and related disorders in a manner similar to that used for melatonin.

However, it will be understood that the amount of the compound actually administered will be determined by a physician, in light of the relevant circumstances including the condition to be treated, the choice of compound to be administered, the chosen route of administration, the age, weight and response of the individual patient, and the severity of the patient's symptoms.

The compounds which constitute this invention, their methods of preparation and their biologic actions will appear more fully from consideration of the following examples, which are given for the purpose of illustration only and are not to be construed as limiting the invention in sphere or scope.

DESCRIPTION OF SPECIFIC EMBODIMENTS

Intermediates 2 to 15d illustrated in Reaction Schemes 1 to 3 above were made in accordance with the experimentals below. The intermediates were then used to synthesize Examples 1 to 98.

In the following intermediates and examples, used to illustrate the foregoing synthetic processes, all temperatures are expressed in degrees Celsius and melting points are uncorrected. Proton magnetic resonance ($^1$H NMR) and carbon magnetic resonance ($^{13}$C NMR) spectra were determined in the solvents indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dt, doublet of triplet; bs, broad singlet; dq, doublet quartet. The infrared (IR) spectral descriptions include only absorption wave numbers (cm$^{-1}$) having functional group identification value. The IR determinations were employed using the compound neat as a film or by employing potassium bromide (KBr) as diluent. Optical rotations $[\alpha]_D^{25}$ were determined in the solvents and concentration indicated. Low resolution mass spectra (MS) are reported as the apparent molecular weight (M+H)$^+$. The elemental analyses are reported as percent by weight.

Intermediate 2

(2E)-3-(2-Hydroxy-3-nitrophenyl)prop-2-enenitrile

Diethyl cyanomethyl phosphonate (21.24 g) was added dropwise to a suspension of NaH (7.2 g, 60%) in THF (200 mL) at 0° C. After stirring for 1 h, a solution of 3-nitrosalicylaldehyde 1 (10 g) in THF (40 mL) was added. The resulting mixture was stirred for 1 h and quenched with water. After the THF was removed, the residue was extracted with EtOAc. The combined organic layer was dried over MgSO$_4$, filtered and concentrated to give a residue. The residue was purified by flash chromatography over silica gel (elution with dichloromethane) to give 11 g (95%) of the desired compound 2.

IR (film, cm$^{-1}$) 3228 (br), 2221; $^1$H NMR (300 MHz, CDCl$_3$): δ8.20 (dd, J=8.4, 1.6 Hz, 1H), 7.73–7.70 (m, 1H), 7.64 (d, J=16.8 Hz, 1H), 7.08 (t, =7.7 Hz, 1H), 6.26 (d, J=16.8 Hz, 1H); $^{13}$C NMR (75 MHz,CDCl$_3$) δ153.8, 143.7, 136.4, 134.3, 127.3, 125.0, 120.1, 118.0, 100.6; MS(ESI) 189 (M–H)$^+$.

Intermediate 3a

N-[3-(2-Cyanoethyl)-2-hydroxyphenyl]propanamide

A suspension of 2 (5.044 g), 10% Pd/C (1 g), and (EtCO)$_2$O (5.004 g) was hydrogenated at 50 psi for 16 h. After filtration, the filtrate was quenched with 10N NaOH. After the THF was removed, the residue was acidified and extracted with EtOAc. The combined organic layer was dried over MgSO$_4$, filtered and concentrated to give a residue. The residue was purified by flash chromatography over silica gel (elution with 30% EtOAc/hexanes) to give 5.5 g (97%) of the desired compound 3a.

IR (film, cm$^{-1}$) 3283 (br), 1637; $^1$H NMR (300 MHz, CDCl$_3$): δ9.41 (s, 1H), 7.87 (br s, 1H), 7.03–6.93 (m, 1H), 6.75–6.69 (m, 2H), 2.97 (t, J=7.0 Hz, 2H), 2.69 (t, J=7.0 Hz, 2H), 2.44 (q, J=7.5 Hz, 2H), 1.22 (t, J=7.5 Hz, 3H); $^{13}$C NMR (75 MHz,CDCl$_3$) δ175.0, 147.5, 129.0, 128.2, 125.9, 121.9, 120.2, 120.0, 29.8, 27.5, 17.4, 9.9; MS(ESI) 217 (M–H)$^+$.

Intermediate 3b

N-[3-(2-Cyanoethyl)-2-hydroxyphenyl]butanamide

The compound was prepared by the general procedure described in 3a using 2 (1940 mg), 10% Pd/C (400 mg), and (n-PrCO)$_2$O (2 g). Purification by flash chromatography over silica gel (elution with 30% EtOAc/hexanes) gave 1856 mg (80%) of the desired product.

IR (film, cm$^{-1}$) 3307(br), 1644; $^1$H NMR (300 MHz, CDCl$_3$): δ7.07–7.05 (m, 1H), 6.82–6.75 (m, 2H), 3.03 (t, J=7.1 Hz, 2H), 2.75 (t, J=7.0 Hz, 2H), 2.49 (t, J=8.9 Hz, 2H), 1.82–1.70 (m, 2H), 1.04 (t, J=7.3 Hz, 3H); $^{13}$C NMR (75 MHz,CDCl$_3$) δ174.3, 147.7, 129.2, 128.3, 126.0, 121.9, 120.3, 120.1, 38.7, 27.6, 19.4, 17.5, 13.7; MS(ESI) 231 (M–H)$^+$; Anal Calcd for C$_{13}$H$_{16}$N$_2$O$_2$ C, 67.22; H, 6.94. Found: C, 67.25; H, 6.92.

Intermediate 3c

N-[3-((1E)-2-Cyanoethyl)-2-hydroxyphenyl]-2-methylpropanamide

The compound was prepared by the general procedure described in 3a using 2 (2.53 g), 10% Pd/C (0.5 g), and isobutyric anhydride (4.21 g). Purification by flash chromatography over silica gel, elution with 30% EtOAc/hexanes, gave 2.18 g (71%) of the desired product.

$^1$H NMR (300 MHz, CDCl$_3$) δ7.44 (br, s, 1H), 7.10 (dd, J=6.6, 2.4 Hz, 1H), 6.86–6.78 (m, 2H), 3.02 (t, J=7.2 Hz, 2H), 2.75–2.62 (m, 3H), 1.31 (d, J=6.9 Hz, 6H); $^{13}$C NMR (75 MHz, CDCl$_3$) δ177.9, 147.6, 129.4, 128.3, 125.7, 121.6, 120.1, 120.0, 36.1, 27.6, 19.7, 17.3; MS (ESI): 233 (M+H)$^+$.

Intermediate 3d

N-[3-((1E)-2-Cyanoethyl)-2-hydroxyphenyl]-5-phenylpentanamide

A suspension of 2 (5.7 g), 10% Pd/C (1 g), and $(EtCO)_2O$ (5.004 g) was hydrogenated at 50 psi for 16 h to yield (t-butoxy)-N-[3-(2-cyanoethyl)-2-hydroxyphenyl] carboxamide, Intermediate 6 below. Purification by flash chromatography over silica gel eluting with EtOAc gave 7.4 g (94%) of product. A mixture of 15 (7.205 g) and 60 mL of 4 N HCl in EtOAc (100 mL) at 40° C. was stirred for 2 h. After cooling to rt, the mixture was diluted with ether and based to neutral. The organic layer was washed with brine, dried with $MgSO_4$, concentrated to give 2.0 g (45%) of a crude product that was used in the next step without purification. A solution of 5-phenyl valeryl chloride (576 mg) in methylene chloride (1 mL) was added a solution of the above product (486 mg) and $Et_3N$ (606 mg) in methylene chloride (6 mL). After stirring for 1 h, purification by flash chromatography over silica gel (elution with 50% EtOAc/hexanes) gave 786 mg (81%) of the desired product.

IR (film, cm$^{-1}$) 3307(br), 1644; $^1$H NMR (300 MHz, CDCl$_3$): δ7.61 (s, 1H), 7.54–7.06 (m, 6H), 6.91–6.72 (m, 2H), 3.03 (t, J=7.3 Hz, 2H), 2.80–2.65 (m, 4H), 2.48 (t, J=5.5 Hz, 2H), 1.29–1.24 (m, 4H); $^{13}$C NMR (75 MHz,CDCl$_3$) δ174.0, 147.7, 142.0, 129.3, 128.6, 128.5, 126.1, 126.0, 125.8, 121.8, 120.3, 120.0, 36.8, 35.7, 30.9, 27.7, 25.5, 17.5; MS(ESI) 321 (M–H)$^+$.

Intermediate 3e

N-[3-((1E)-2-Cyanoethyl)-2-hydroxyphenyl]benzamide

The title compound was prepared by the general procedure described in 3a using 2 (1940 mg), 10% Pd/C (400 mg), and (PhCO)$_2$O (4.2 g). Purification by flash chromatography over silica gel (elution with 50% EtOAc/hexanes) gave 2632 mg (99%) of the desired product.

IR (film, cm$^{-1}$) 3315(br), 1637; $^1$H NMR (300 MHz, CDCl$_3$): δ8.22 (br s, 1H), 7.89 (dd, J=7.0, 1.4 Hz, 1H), 7.62–7.47 (m, 3H), 7.11 (d, J=7.2 Hz, 1H), 6.95 (dd, J=8.0, 1.6 Hz, 1H), 6.86 (t, J=7.9 Hz, 1H), 3.04 (t, J=7.2 Hz, 2H), 2.73 (t, J=7.2 Hz, 2H); $^{13}$C NMR (75 MHz,CDCl$_3$) δ167.7, 147.8, 132.8, 132.7, 129.4, 129.1, 128.6, 127.5, 125.8, 122.3, 120.4, 119.9, 27.6, 17.5; MS(ESI) 265 (M–H)$^+$.

Intermediate 3f 3-(2-Acetoxy-3-acetamidophenyl)propanenitrile

A solution of 2 (3.49 g, 18.4 mmol) in Ac$_2$O (150 mL) containing 10% Pd/C (2.0 g) was hydrogenated in a Parr apparatus at 50 psi for 2 h. The catalyst was then removed by filtration over Celite, and the filtrate was poured gradually into 2 N NaOH (1.0 L), and stirred until the anhydride was completely hydrolyzed, as evidenced by the formation of a single phase. The solution was cooled to room temperature, and was extracted with CH$_2$Cl$_2$. The organic extract was dried (Na$_2$SO$_4$), and was then subjected to chromatography (SiO$_2$:CH$_2$Cl$_2$/MeOH/30% aq NH$_3$ 95/4.5/0.5). After solvent removal, the residue was triturated in CH$_2$Cl$_2$:Et$_2$O 1:1, collecting a white solid in two crops to afford 2.58 g (57% yield): MS (ESI) m/z 245.22 (MH$^-$); IR (KBr) 2247 cm$^{-1}$; $^1$H NMR (CDCl$_3$) δ7.95 (d, 1H, J=8.1 Hz), 7.25 (t, 1H, J=7.8 Hz), 7.08 (m, 2H), 2.86 (t, 2H, J=7.5 Hz), 2.59 (t, 2H, J=7.5 Hz), 2.42 (s, 3H), 2.18 (s, 3H); $^{13}$C NMR (CDCl$_3$) δ168.9, 168.5, 140.2, 131.0, 130.7, 127.3, 126.0, 123.6, 119.0, 26.7, 24.6, 20.9, 17.9; Anal. Calcd for C$_{13}$H$_{14}$N$_2$O$_3$.0.2 H$_2$O: C, 62.49; H, 5.81; N, 11.21. Found: C, 62.59; H, 5.83; N, 10.81.

Intermediate 4a 3-(2-Ethylbenzoxazol-7-yl)propanenitrile

A solution of 3a (1.5 g) and PPTS (500 mg) in xylene (40 mL) was refluxed for 2 h. After cooling to rt, the reaction was quenched with water and diluted with EtOAc. The organic layer was dried over MgSO$_4$, filtered and concentrated to give a residue. The residue was purified by flash chromatography over silica gel (elution with 50% EtOAc/hexanes) to give 1.33 g (95%) of the desired compound.

IR (film, cm$^{-1}$) 3224, 1612; $^1$H NMR (300 MHz, CDCl$_3$): δ7.58 (dd, J=7.8, 1.1 Hz, 1H), 7.25 (t, J=7.8 Hz, 1H), 7.15 (dd, J=7.5, 0.5 Hz, 1H), 3.23 (t, J=7.4 Hz, 2H), 3.01 (q, J=7.5 Hz, 2H), 2.71 (t,=7.5 Hz, 2H), 1.46 (t, J=7.5 Hz, 3H); $^{13}$C NMR (75 MHz,CDCl$_3$) δ168.1, 149.2, 141.6, 124.6, 124.5, 120.9, 118.9, 118.8, 32.1, 23.6, 17.8, 11.0; MS(ESI) 200 (M)$^+$.

Intermediate 4b 3-(2-Propylbenzoxazol-7-yl)propanenitrile

The title compound was prepared by the general procedure described in 4a using 3b (1500 mg) PPTS (487 mg). Purification by flash chromatography over silica gel (elution with 50% EtOAc/hexanes) gave 1313 mg (95%) of the desired product.

IR (film, cm$^{-1}$) 3455; $^1$H NMR (300 MHz, CDCl$_3$): δ7.61 (dd, J=7.8, 1.1 Hz, 1H), 7.29 (t, J=7.7 Hz, 1H), 7.17 (d, J=7.3 Hz, 1H), 3.26 (t, J=7.5 Hz, 2H), 2.95 (q, J=7.4 Hz, 2H), 2.78 (t,=7.5 Hz, 2H), 2.04–1.87 (m, 2H), 1.09 (t, J=7.4 Hz, 3H); $^{13}$C NMR (75 MHz,CDCl$_3$) δ167.3, 149.3, 141.5, 124.8, 124.7, 121.0, 119.0, 118.9, 30.6, 26.4, 20.4, 17.9, 13.9;

MS(ESI) 213 (M–1)$^+$; Anal Calcd for C$_{13}$H$_{14}$N$_2$O C, 72.87; H, 6.59. Found: C, 72.70; H, 6.60.

Intermediate 4c

3-[2-(Methylethyl)benzoxazol-7-yl]propanenitrile

The title compound was prepared by the general procedure described in 4a using 3c (2.08 g), PPTS (0.68 g). Purification by flash chromatography over silica gel, elution with 30% EtOAc/hexanes, gave 1.84 g (96%) of desired product.

$^1$H NMR (300 MHz, CDCl$_3$) δ7.59 (d, J=7.2 Hz, 1H), 7.25 (t, J=7.7 Hz, 1H). 7.15 (d, J=7.4 Hz, 1H), 3.29–3.18 (m, 3H), 2.77 (t, J=7.4 Hz, 2H), 1.46 (d, J=7.0 Hz, 6H); $^{13}$C NMR (75 MHz, CDCl$_3$) δ171.2, 149.0, 141.3, 124.5, 124.4, 120.8, 118.7, 118.6, 28.8, 26.2, 20.2, 17.6; MS (ESI): 215 (M+H)$^+$.

Intermediate 4d

3-[2-(4-Phenylbutyl)benzoxazol-7-yl]propanenitrile

The title compound was prepared by the general procedure described in 4a using 3d (750 mg) and PPTS (175 mg). Purification by flash chromatography over silica gel (elution with 50% EtOAc/hexanes) gave 670 mg (95%) of the desired product.

IR (film, cm$^{-1}$) 2247; $^1$H NMR (300 MHz, CDCl$_3$): δ7.62 (d, J=7.8 Hz, 1H), 7.31–7.06 (m, 7H), 3.26 (t, J=7.5 Hz, 2H), 3.02 (t, J=7.3 Hz, 2H), 2.94–2.78 (m, 4H), 1.96–1.74 (m, 4H); $^{13}$C NMR (75 MHz, CDCl$_3$) δ167.2, 149.2, 142.0, 141.3, 128.6, 128.5, 126.0, 124.9, 124.8, 121.1, 119.0, 118.8, 35.6, 31.0, 28.6, 26.5, 26.4; MS(ESI) 303 (M−H)$^+$.

Anal Calcd for C$_{20}$H$_{20}$N$_2$O C, 78.92; H, 6.62; Found: C, 78.78; H, 6.60.

Intermediate 4e

3-(2-Phenylbenzoxazol-7-yl)propanenitrile

The title compound was prepared by the general procedure described in 4a using 3e (19950 mg) and PPTS (565 mg). Purification by flash chromatography over silica gel (elution with 30% EtOAc/hexanes) gave 1786 mg (96%) of the desired product.

IR (film, cm$^{-1}$) 2247; $^1$H NMR (300 MHz, CDCl$_3$): δ8.27–8.21 (m, 2H), 7.70 (dd, J=7.9, 1.1 Hz, 1H), 7.56–7.34 (m, 3H), 7.31 (t, J=7.2 Hz, 1H), 7.22 (t, J=6.6 Hz, 1H), 3.34 (t, J=7.5 Hz, 2H), 2.86 (t, J=7.5 Hz, 2H); $^{13}$C NMR (75 MHz,CDCl$_3$) δ163.0, 149.1, 142.3, 131.8, 129.0, 127.7, 126.9, 125.3, 125.1, 121.2, 119.3, 118.9, 26.4, 17.8; MS(ESI) 247 (M−H)$^+$.

Intermediate 4f

3-(2-Hydroxy-3-acetamidophenyl)propanamine

A solution of 3f (2.58 g, 10.5 mmol) in 200 mL of MeOH:30% aq NH$_3$ (85:15) containing Raney nickel was hydrogenated in a Parr apparatus at 50 psi for 1 h. The catalyst was removed by filtration over Celite, and the solvent was removed in vacuo. The residue was taken up in CH$_2$Cl$_2$ and the resulting solution was dried (Na$_2$SO$_4$), followed by the addition of ether. A light gray solid was isolated by filtration to furnish 1.7 g (78% yield).

MS (ESI) m/z 209.17 (MH$^+$); $^1$H NMR (DMSO-d$_6$) δ9.03 (br s, 1H), 7.73 (d, 1H, J=7.5 Hz), 6.72 (d, 1H, J=7.2 Hz), 6.52 (t, 1H, J=7.5 Hz), 6.16 (br s, 3H), 2.63 (m, 2H), 2.49 (m, 2H), 2.06 (s, 3H), 1.72 (m, 2H); $^{13}$C NMR (DMSO-d$_6$) δ168.1, 149.1, 127.7, 127.6, 127.4, 124.9, 118.0, 116.5, 37.5, 26.5, 24.1, 14.0; Anal. Calcd for C$_{11}$H$_{16}$N$_2$O$_2$.0.2 H$_2$O: C, 62.36; H, 7.80; N, 13.22; Found: C, 62.33; H, 7.75; N, 13.11.

Intermediate 5a

3-(2-Ethylbenzoxazol-7-yl)propylamine

A suspension of 4a (1.25 g) and Raney Nickel (1 mL) in MeOH/NH$_3$.H$_2$O(50/15 mL) was hydrogenated at 50 psi for 1.5 h. After filtration, the MeOH was removed. The residue was extracted with EtOAc. The organic layer was dried over MgSO$_4$, filtered and concentrated to give 1.25 g (99%) of the desired product which was used in the next step without purification.

$^1$H NMR (300 MHz, CDCl$_3$): δ7.52 (dd, J=7.8, 0.5 Hz, 1H), 7.25 (t, J=7.6 Hz, 1H), 7.11 (d, J=7.4 Hz, 1H), 3.00–2.82(m, 6H), 2.04–1.86 (m, 2H), 1.48 (t,=7.5 Hz, 3H).

Intermediate 5b

3-(2-Propylbenzoxazol-7-yl)propylamine

The title compound was prepared by the general procedure described in 5a using 4b (1284 mg). Work-up gave 1.30 g (100%) of the desired product which was used in the next step without purification.

Intermediate 5c

3-[2-(Methylethyl)benzoxazol-7-yl]propylamine

The title compound was prepared by the general procedure described in 5a using 4c (1.78 g), Raney Nickel (1 ml) in MeOH/NH$_3$.H$_2$O (70/20 ml) to give 1.81 g (100%) of crude product.

MS (ESI): 219 (M+H)$^+$.

Intermediate 5d

3-[2-(4-Phenylbutyl)benzoxazol-7-yl]propylamine

The title compound was prepared by the general procedure described in 5a using 4d (670 mg). Work-up gave 640 mg (95%) of the desired product which was used in the next step without purification.

Intermediate 5e

3-(2-Phenylbenzoxazol-7-yl)propylamine

The title compound was prepared by the general procedure described in 5a using 4e (1480 mg). Work-up gave 1500 mg (100%) of the desired product which was used in the next step without purification.

Intermediate 5f

2-Methyl-7-(3-aminopropyl)benzoxazole

A solution of 4f (1.5 g, 7.2 mmol) and pyridinium p-toluenesulfonate (450 mg, 1.8 mmol) in xylene (250 mL) was refluxed overnight, using a Dean-Stark trap. The resulting solution was poured hot over a silica gel bed, eluting with CH$_2$Cl$_2$:MeOH:30% aq NH$_3$ (96:3.6:0.4). After solvent removal, the residue was taken up in a minimum of CH$_2$Cl$_2$, to which 1N HCl/Et$_2$O (5 mL) was added, resulting in the formation of a precipitate. The precipitate was collected by filtration to afford a white solid (0.69 g, 43% yield).

MS (ESI) m/z 191.20 (MH$^+$); $^1$H NMR (DMSO-d$_6$) δ8.13 (br s, 3H), 7.49 (d, 1H, J=7.5 Hz), 7.22 (m, 2H), 2.90 (m, 2H), 2.76 (m, 2H), 2.60 (s, 3H), 2.00 (m, 2H); $^{13}$C NMR (DMSO-d$_6$) δ163.6, 149.0, 124.5, 124.3, 123.7, 117.0, 38.4, 27.0, 26.3, 14.2; Anal. Calcd for C$_{11}$H$_{14}$N$_2$O.HCl.0.5 H$_2$O: C, 56.05; H, 6.41; N, 11.88; Found: C, 55.74; H, 6.52; N, 11.79.

Intermediate 6

(t-Butoxy)-N-[3-(2-cyanoethyl)-2-hydroxyphenyl] carboxamide

A suspension of 2 (5.7 g), 10% Pd/C (1 g), and (EtCO)$_2$O (5.004 g) was hydrogenated at 50 psi for 16 h to yield (t-butoxy)-N-[3-(2-cyanoethyl)-2-hydroxyphenyl] carboxamide. Purification by flash chromatography over silica gel eluting with EtOAc gave 7.4 g (94%) of product.

IR (film, cm$^{-1}$) 3312, 1678; $^1$H NMR (300 MHz, CDCl$_3$): δ7.04(dd, J=7.5, 0.8 Hz, 1H), 6.88–6.75 (m, 2H), 3.03(t, J=7.3 Hz, 2H), 2.73(t, J=7.3 Hz, 2H), 1.54(s, 9H); $^{13}$C NMR (75 MHz,CDCl$_3$) δ155.9, 146.9, 129.0, 127.5, 125.5, 121.6, 120.6, 119.9, 83.0, 28.6, 27.6, 17.6; MS(ESI) 261 (M−H)$^+$.

Intermediate 7a

N-(3-{3-[(t-Butoxy)carbonylamino]-2-hydroxyphenyl}propyl)acetamide

The title compound was prepared by the general procedure described above using 6 (1.04 g), Raney-nickel (2 mL), and (MeCO)$_2$O (2 mL). Purification by flash chromatography over silica gel (elution with EtOAc) gave 400 mg (32%) of the desired compound.

IR (film, cm$^{-1}$) 3312, 1678; $^1$H NMR (300 MHz, CDCl$_3$): δ7.04(d, J=7.7 Hz, 1H), 6.88–6.75 (m, 2H), 3.24(q, J=6.1 Hz, 2H), 2.73 (t, J=6.9 Hz, 2H), 2.05 (s, 3H), 1.85–1.77 (m, 2H), 1.52 (s, 9H); $^{13}$C NMR (75 MHz,CDCl$_3$) δ171.2, 155.0, 145.5, 130.6, 126.7, 126.1, 120.7, 119.0, 81.7, 38.8, 31.0, 28.4, 27.2, 23.5; MS(ESI) 307 (M–H)$^+$.

Intermediate 7b

N-(3-{3-[(t-Butoxy)carbonylamino]-2-hydroxyphenyl}propyl)propanamide

The title compound was prepared by the general procedure described above using 6 (1.04 g), Raney-nickel (2 mL), and (EtCO)$_2$O (2 mL). Purification by flash chromatography over silica gel (elution with EtOAc) gave 350 mg (27%) of the desired compound.

IR (film, cm$^{-1}$) 3302, 1678; $^1$H NMR (300 MHz, CDCl$_3$): δ7.04(dd, J=7.7, 0.8 Hz, 1H), 6.88–6.78 (m, 2H), 3.24 (q, J=6.1 Hz, 2H), 2.73 (t, J=6.6 Hz, 2H), 2.27 (q, J=7.5 Hz, 2H), 1.85–1.77 (m, 2H), 1.52 (s, 9H), 1.19 (t, J=7.5 Hz, 3H); $^{13}$C NMR (75 MHz,CDCl$_3$) δ175.0, 154.9, 145.4, 130.5, 126.8, 126.0, 120.7, 118.8, 81.6, 38.6, 31.5, 30.0, 28.4, 27.2, 10.0; MS(ESI) 321 (M–H)$^+$.

Intermediate 7c

N-(3-{3-[(t-Butoxy)carbonylamino]-2-hydroxyphenyl}propyl)-2-methylpropanamide

The title compound was prepared by the general procedure described above using 6 (1.04 g), Raney-nickel (2 mL), and (i-PrCO)$_2$O (2 mL). Purification by flash chromatography over silica gel (elution with EtOAc) gave 375 mg (28%) of the desired compound.

IR (film, cm$^{-1}$) 3305, 1670; $^1$H NMR (300 MHz, CDCl$_3$): δ7.04(dd, J=7.6, 1.8 Hz, 1H), 6.88–6.78 (m, 2H), 3.24 (q, J=6.1 Hz, 2H), 2.71 (t, J=6.5 Hz, 2H), 2.42–2.33 (m, 1H), 1.87–1.73 (m, 2H), 1.52 (s, 9H), 1.26 dt, J=8.0 Hz, 6H); $^{13}$C NMR (75 MHz,CDCl$_3$) δ178.2, 154.8, 145.3, 130.4, 126.9, 125.9, 120.7, 118.6, 81.5, 38.4, 36.0, 31.8, 28.4, 27.1, 19.8; MS(ESI) 335 (M–H)$^+$.

Intermediate 8a

N-[3-(3-Amino-2-hydroxyphenyl)propyl]acetamide

A mixture of 7a (308 mg) and 2 mL of 6N HCl in EtOAC (10 mL) was stirred at 40° C. for 1 h. After cooling, the reaction mixture was neutralized with 1 N NaOH. Work-up gave 139 mg (67%) of the desired product that was used in the next step without purification.

$^1$H NMR (300 MHz, CDCl$_3$): δ6.73–6.52 (m, 3H), 3.22 (m, 2H), 2.65 (t, J=7.0 Hz, 2H), 1.94 (s, 3H) 1.82–1.73 (m, 2H).

Intermediate 8b

N-[3-(3-Amino-2-hydroxyphenyl)propyl]propanamide

A mixture of 7b (322 mg) and 2 mL of 6N HCl in EtOAC (10 mL) was stirred at 40° C. for 1 h. After cooling, the reaction mixture was neutralized with 1 N NaOH. Work-up gave 144 mg (65%) of the desired product that was used in the next step without purification or analysis.

Intermediate 8c

N-[3-(3-Amino-2-hydroxyphenyl)propyl]-2-methylpropanamide

A mixture of 7c (336 mg) and 2 mL of 6N HCl in EtOAC (10 mL) was stirred at 40° C. for 1 h. After cooling, the reaction mixture was neutralized with 1 N NaOH. Work-up gave 170 mg (72%) of the desired product that was used in the next step without purification.

$^1$H NMR (300 MHz, CDCl$_3$): δ6.73–6.46 (m, 3H), 3.28 (m, 2H), 2.67 (t, J=6.5 Hz, 2H), 2.44–2.31 (m, 1H) 1.82–1.73 (m, 2H), 1.21 (d, J=6.0 Hz, 6H).

Intermediate 9

Ethyl (2E)-3-(2-hydroxy-3-nitrophenyl)prop-2-enoate

A solution of 3-nitrosalicylaldehyde (20 g) and Ph$_3$PCHCO$_2$Et (63 g) in THF (300 mL) was refluxed for 2 h. After concentration, the residue was purified by flash chromatography over silica gel (elution with CH$_2$Cl$_2$) to give 25.6 g (90%) of the desired compound. No analysis was undertaken.

Intermediate 10

Ethyl (1R,2R)-2-(2-hydroxy-3-nitrophenyl)cyclopropanecarboxylate

Methyl-3-nitro-1-nitrosoquanidine (73 g) was carefully added to a mixture of 10 N NaOH (200 mL) and ether (640 mL) at 0° C. portionwise. After stirring for 0.5 h, the ether layer was decanted into a solution of 9 (10.65 g) and Pd(OAc)$_2$ (1 g) at 0° C. After stirring for 0.5 h and filtering, the filtrate was concentrated and purified by flash chromatography over silica gel (elution with 10% EtOAc/hexanes) to give 8 g (70%) of the desired compound.

IR (film, cm$^{-1}$) 3218, 1724; $^1$H NMR (300 MHz, CDCl$_3$): δ7.99 (d, J=8.5 Hz, 1H), 7.27 (d, J=7.5 Hz, 1H), 6.97 (t, J=8.4 Hz, 1H), 4.23 (q, J=7.1 Hz, 2H), 2.80–2.73 (m, 1H), 1.90–1.84 (m, 1H), 1.71–1.60 (m, 1H), 1.38–1.31 (m, 1H), 1.08 (t, J=7.1 Hz, 3H); $^{13}$C NMR (75 MHz,CDCl$_3$) δ173.2, 154.5, 134.2, 133.7, 131.4, 123.4, 119.5, 61.0, 22.8, 20.7, 15.3, 14.4; MS(ESI) 250 (M–H)$^+$.

Intermediate 11a

Ethyl (1R,2R)-2-[2-hydroxy-3-(propanoylamino)phenyl]cyclopropanecarboxylate

The title compound was prepared by the general procedure described in 3a using 10 (2.27 g), 10% Pd/C (400 mg), and (EtCO)$_2$O (5.004 g). Purification by flash chromatography over silica gel (elution with 10% EtOAc/hexanes) gave 2.37 g (94%) of the desired compound.

IR (film, cm$^{-1}$) 3212, 1704; $^1$H NMR (300 MHz, CDCl$_3$): δ6.93–6.87 (m, 1H), 6.76–6.70 (m, 1H), 4.17 (q, J=7.1 Hz, 2H), 2.80–2.73 (m, 1H), 2.49 (q, J=7.5 Hz, 2H), 1.88–1.82 (m, 1H), 1.54–1.46 (m, 1H), 1.31–1.01 (m, 7H); $^{13}$C NMR (75 MHz,CDCl$_3$) δ174.5, 174.0, 148.0, 130.3, 125.8, 123.8, 120.7, 120.0, 60.8, 30.1, 22.8, 21.6, 15.7, 14.3, 14.2, 9.9; MS(ESI) 276 (M–H)$^+$.

Intermediate 11b

Ethyl (1R,2R)-2-[3-(butanoylamino)-2-hydroxyphenyl]cyclopropanecarboxylate

The title compound was prepared by the general procedure described in 11a using 10 (2.51 g), 10% Pd/C (0.5 g), and n-butyric anhydride (1.74 g). Purification by flash chromatography over silica gel, elution with 30% EtOAc/hexanes, gave 2.45 g (84%) of desired product.

$^1$H NMR (300 MHz, CDCl$_3$) δ8.92 (br, s, 1H), 8.25 (br, s, 1H), 6.90 (dd, J=5.6, 3.9 Hz, 1H), 6.75–6.70 (m, 2H), 4.15

(q, J=7.1 Hz, 2H), 2.84–2.75 (m, 1H), 2.40 (t, J=7.4 Hz, 2H), 1.91–1.83 (m, 1H), 1.78–1.67 (m, 2H), 1.58–1.51 (m, 1H), 1.35–1.23 (m, 1H), 1.26 (t, J=7.1 Hz, 3H), 0.97 (t, J=7.4 Hz, 3H); $^{13}$C NMR (75 MHz, CDCl$_3$) δ173.9, 173.8, 148.0, 130.1, 125.8, 123.7, 120.7, 119.8, 60.6, 38.6, 22.7, 21.5, 19.2, 15.6, 14.2, 13.5; MS (ESI): 292 (M+H)$^+$.

Intermediate 11c

Ethyl (1R,2R)-2-[2-hydroxy-3-(2-methylpropanoylamino)phenyl]cyclopropanecarboxylate The title compound was prepared by the general procedure described in 11a using 10 (2.51 g), 10% Pd/C (0.5 g), and isobutyric anhydride (1.74 g). Purification by flash chromatography over silica gel, elution with 30% EtOAc/hexanes, gave 2.31 g (79%) of desired product.

$^1$H NMR (300 MHz, CDCl$_3$) δ8.82 (br, s, 1H), 8.25 (br, s, 1H), 6.93 (dd, J=6.2, 3.3 Hz, 1H), 6.78–6.75 (m, 2H), 4.17 (q, J=7.1 Hz, 2H), 2.83–2.76 (m, 1H), 2.72–2.59 (m, 1H), 1.90–1.83 (m, 1H), 1.61–1.53 (m, 1H), 1.38–1.23 (m, 10H); $^{13}$C NMR (75 MHz, CDCl$_3$) δ177.5, 173.8, 148.0, 130.2, 125.7, 123.8, 120.5, 119.9, 60.6, 36.0, 22.6, 21.5, 19.6, 15.5, 14.2; MS (ESI): 292 (M+H)$^+$.

Intermediate 11d

Ethyl (1R,2R)-2-[2-hydroxy-3-(5-phenylpentanoylamino)phenyl]cyclopropanecarboxylate A suspension of Raney-nickel (1 mL) and 10 (1135 mg) in THF was hydrogenated at 50 psi for 2 h. After filtration, the filtrate was concentrated to give 985 mg (100%) of a crude product that was used in the next step without purification. The title compound was prepared by the general procedure described above using the above crude product 985 mg), Ph(CH$_2$)$_4$COCl (960 mg), and Et$_3$N (101 mg). Purification by flash chromatography over silica gel (elution with 30% EtOAc/hexanes) gave 1749 mg (98%) of the desired compound.

IR (film, cm$^{-1}$) 3308, 1724; $^1$H NMR (300 MHz, CDCl$_3$): δ7.32–7.17 (m, 5H), 6.90–6.74 (m, 2H), 4.21 (q, J=7.1 Hz, 2H), 2.80–2.76 (m, 1H), 2.69(t, J=7.3 Hz, 2H), 2.48 (t, J=7.0 Hz, 2H), 2.05–1.56 (m, 6H), 1.33–1.07 (m, 4H); $^{13}$C NMR (75 MHz,CDCl$_3$) δ173.9, 173.5, 148.1, 142.0, 130.5, 128.6, 126.1, 125.8, 124.1, 120.6, 120.1, 60.8, 37.0, 35.7, 31.0, 25.5, 22.8, 21.6, 15.8, 14.4; MS(ESI) 380 (M–H)$^+$.

Intermediate 12a

Ethyl (1R,2R)-2-(2-ethylbenzoxazol-7-yl)cyclopropanecarboxylate

The title compound was prepared by the general procedure described in 4a using 11a (2.043 g) and PPTS (678 mg). Purification by flash chromatography over silica gel (elution with 30% EtOAc/hexanes) gave 1626 mg (90%) of the desired product.

$^1$H NMR (300 MHz, CDCl$_3$): δ7.52 (dd, J=7.9, 1.0 Hz, 1H), 7.25 (d, J=7.8 Hz, 1H), 6.97 (d, J=7.5 Hz, 1H), 4.23 (q, J=7.1 Hz, 2H), 3.00 (q, J=7.5 Hz, 2H), 2.80–2.73 (m, 1H), 2.21–2.15 (m, 1H), 1.67–1.60 (m, 1H), 1.58–1.41 (m, 1H), 1.47 (t, J=7.5 Hz, 3H), 1.12 (t, J=7.1 Hz, 3H); $^{13}$C NMR (75 MHz,CDCl$_3$) δ173.3, 168.2, 149.2, 141.1, 124.3, 123.8, 121.9, 117.5, 60.9, 22.9, 22.2, 21.6, 16.2, 14.3, 11.0; MS(ESI) 260 (M+H)$^+$.

Intermediate 12b

Ethyl (1R,2R)-2-(2-propylbenzoxazol-7-yl)cyclopropanecarboxylate

The title compound was prepared by the general procedure described in 12a using 11b (2.37 g), PPTS (0.60 g). Purification by flash chromatography over silica gel, elution with 30% ETOAc/hexanes, gave 1.93 g (87%) of desired product.

$^1$H NMR (300 MHz, CDCl$_3$) δ7.50 (d, J=7.9 Hz, 1H), 7.19 (t, J=7.8 Hz, 1H). 6.96 (d, J=7.6 Hz, 1H), 4.19 (q, J=7.1 Hz, 2H), 2.90 (t, J=7.4 Hz, 2H), 2.82–2.74 (m, 1H), 2.22–2.16 (m, 1H), 1.98–1.26 (m, 2H), 1.71–1.64 (m, 1H), 1.61–1.54 (m, 1H), 1.29 (t, J=7.1 Hz, 3H), 1.05 (t, J=7.4 Hz, 3H); $^{13}$C NMR (75 MHz, CDCl$_3$) δ173.3, 167.0, 149.1, 141.4, 124.0, 123.6, 124.7, 117.4, 60.7, 30.4, 22.7, 21.5, 20.2, 16.0, 14.2, 13.6; MS (ESI): 274 (M+H)$^+$.

Intermediate 12c

Ethyl (1R,2R)-2-[2-(methylethyl)benzoxazol-7-yl]cyclopropanecarboxylate

The title compound was prepared by the general procedure described in 12a using 11c (2.21 g), PPTS (0.57 g). Purification by flash chromatography over silica gel, elution with 30% EtOAc/hexanes, gave 1.97 g (95%) of desired product.

$^1$H NMR (300 MHz, CDCl$_3$) δ7.52 (d, J=7.8 Hz, 1H), 7.20 (t, J=7.8 Hz, 1H). 6.97 (d, J=7.6 Hz, 1H), 4.21 (q, J=7.1 Hz, 2H), 3.32–3.17 (m, 1H), 2.82–2.74 (m, 1H), 2.23–2.17 (m, 1H), 1.72–1.66 (m, 1H), 1.62–1.56 (m, 1H), 1.47 (d, J=7.0 Hz, 6H), 1.30 (t, J=7.1 Hz, 3H); $^{13}$C NMR (75 MHz, CDCl$_3$) δ173.2, 171.1, 149.1, 141.3, 124.0, 123.7, 121.7, 117.5, 60.7, 29.8, 22.7, 21.6, 20.2, 16.1, 14.2; MS (ESI): 274 (M+H)$^+$.

Intermediate 12d

Ethyl (1R,2R)-2-[2-(4-phenylbutyl)benzoxazol-7-yl]cyclopropanecarboxylate

The title compound was prepared by the general procedure described in 12a using 11d (1.61 g) and PPTS (339 mg). Purification by flash chromatography over silica gel (elution with 30% EtOAc/hexanes) gave 1370 mg (90%) of the desired product.

$^1$H NMR (300 MHz, CDCl$_3$): δ7.53 (dd, J=7.9, 0.7 Hz, 1H), 7.31–7.13 (m, 6H), 6.99(d, J=7.6 Hz, 1H), 4.25 (q, J=7.1 Hz, 2H), 2.99 (t, J=7.2 Hz, 2H), 2.80–2.76 (m, 1H), 2.75 (t, J=7.5 Hz, 2H), 2.24–2.14 (m, 1H), 2.00–1.53 (m, 6H), 1.38 (t, J=7.1 Hz, 3H); $^{13}$C NMR (75 MHz,CDCl$_3$) δ173.5, 167.1, 149.3, 142.1, 141.5, 128.6, 128.5, 126.0, 124.3, 123.9, 122.0, 117.7, 61.0, 35.6, 31.0, 28.7, 26.5, 23.0, 21.8, 16.3, 14.5.

Intermediate 13a

[(1R,2R)-2-(2-Ethylbenzoxazol-7-yl)cyclopropyl]methan-1-ol

LiAlH$_4$ (152 mg) was added to a solution of 12a (1.036 g) in THF (20 mL). After stirring for 0.5 h, the reaction was quenched using the Fiesher method. The insolubles were removed by filtration and washed with THF. The filtrate was concentrated in vacuo to give a residue. The residue was purified by flash chromatography over silica gel (elution with 33% EtOAc/hexanes) to give 860 mg (99%) of the desired product.

$^1$H NMR (300 MHz, CDCl$_3$): δ7.52 (dd, J=7.9, 1.0 Hz, 1H), 7.25 (d, J=7.8 Hz, 1H), 6.95 (d, J=7.3 Hz, 1H), 3.68–3.63 (m, 2H), 3.06 (q, J=7.5 Hz, 2H), 2.18–2.12 (m, 1H), 1.77–1.66 (m, 1H), 1.51 (t, J=7.5 Hz, 3H), 1.67–1.60 (m, 1H), 1.35–1.21 (m, 1H), 1.09–1.06 (m, 1H); MS(ESI) 218 (M+H)$^+$.

Intermediate 13b

[(1R,2R)-2-(2-Propylbenzoxazol-7-yl)cyclopropyl]methan-1-ol

The title compound was prepared by the general procedure described in 13a using 12b (1.86 g), LAH (0.26 g). Purification by flash chromatography over silica gel, elution with 30% EtOAc/hexanes, gave 1.38 g (86%) of desired product.

$^1$H NMR (300 MHz, CDCl$_3$) δ7.44 (d, J=7.9 Hz, 1H), 7.16 (t, J=7.7 Hz, 1H). 6.88 (d, J=7.6 Hz, 1H), 3.76–3.62 (m, 2H), 2.88 (t, J=7.4 Hz, 2H), 2.34 (br, s, 1H), 2.13–2.07 (m, 1H), 1.97–1.82 (m, 2H), 1.74–1.63 (m, 1H), 1.24–1.1.17 (m, 1H), 1.04 (t, J=7.4 Hz, 3H), 1.09–0.99 (m, 1H); $^{13}$C NMR (75 MHz, CDCl$_3$) δ166.8, 149.3, 140.9, 125.9, 124.0, 121.1, 116.5, 66.1, 30.4, 24.0, 20.2, 16.3, 13.7, 12.5; MS (ESI): 232 (M+H)$^+$.

Intermediate 13c

{(1R,2R)-2-[2-(Methylethyl)benzoxazol-7-yl]cyclopropyl}methan-1-ol

The title compound was prepared by the general procedure described in 13a using 12c (1.87 g), LAH (0.26 g). Purification by flash chromatography over silica gel, elution with 30% EtOAc/hexanes, gave 1.57 g (100%) of desired product.

$^1$H NMR (300 MHz, CDCl$_3$) δ7.47 (d, J=7.9 Hz, 1H), 7.17 (t, J=7.8 Hz, 1H). 6.90 (d, J=7.7 Hz, 1H), 3.77–3.63 (m, 2H), 3.31–3.17 (m, 1H), 2.17–2.08 (m, 2H), 1.77–1.65 (m, 1H), 1.45 (d, J=7.0 Hz, 6H), 1.25–1.19 (m, 1H), 1.07–1.00 (m, 1H); $^{13}$C NMR (75 MHz, CDCl$_3$) δ171.0, 149.2, 140.9, 125.9, 124.0, 121.2, 116.7, 66.2, 28.8, 24.0, 20.3, 16.3, 12.5; MS (ESI): 232 (M+H)$^+$.

Intermediate 13d

{(1R,2R)-2-[2-(4-Phenylbutyl)benzoxazol-7-yl]-cyclopropyl}methan-1-ol

The title compound was prepared by the general procedure described above using 12d (1.3 g) and LiAlH$_4$ (144 mg). Purification by flash chromatography over silica gel (elution with 30% EtOAc/hexanes) gave 1080 mg (96%) of the desired product.

$^1$H NMR (300 MHz, CDCl$_3$): δ7.49 (dd, J=7.9, 1.0 Hz, 1H), 7.31–7.16 (m, 6H), 6.92 (d, J=7.5 Hz, 1H), 3.76–3.62 (m, 2H), 2.98 (t, J=7.3 Hz, 2H), 2.63 (t, J=7.6 Hz, 2H), 2.14–1.68 (m, 6H), 1.26–1.00 (m, 2H); $^{13}$C NMR (75 MHz,CDCl$_3$) δ167.0, 149.5, 142.1, 141.2, 128.6, 128.5, 126.1, 126.0, 124.3, 121.4, 116.8, 66.5, 35.6, 31.0, 28.7, 26.6, 24.3, 16.5, 12.8.

Intermediate 14a

[(1R,2R)-2-(2-Ethylbenzoxazol-7-yl)cyclopropyl]formaldehyde

To a solution of oxalyl chloride (6.4 mol) in CH$_2$Cl$_2$ (8 mL) at −78° C. under N$_2$ was added DMSO (0.57) and stirred for 1 h. A solution of 13a (840 mg) in CH$_2$Cl$_2$ (12 mL) was added dropwise. After stirring for 1 h, the reaction was quenched with Et$_3$N (2.2 mL) and allowed to warm to room temperature, and stirred for 1 h. The reaction was quenched with water. The organic layer was washed with brine, dried over MgSO$_4$, and concentrated in vacuo to give a residue. The residue was purified by flash chromatography over silica gel (elution with 30% EtOAc/hexanes) to give 832 mg (99%) of the desired product.

IR (film, cm$^{-1}$) 1704; $^1$H NMR (300 MHz, CDCl$_3$): δ9.43 (d, J=4.5 Hz, 1H), 7.56 dd, J=8, 1.0 Hz, 1H), 7.25 (d, J=7.8 Hz, 1H), 7.00 (d, J=7.4 Hz, 1H), 3.01 (q, J=7.5 Hz, 2H), 2.90–2.84 (m, 1H), 2.48–2.41 (m, 1H), 1.88–1.77 (m, 1H), 1.49 (t, J=7.5 Hz, 3H); $^{13}$C NMR (75 MHz,CDCl$_3$) δ199.8, 168.3, 149.3, 141.5, 124.4, 122.7, 122.0, 118.1, 32.3, 22.3, 22.1, 15.7, 11.1; MS(ESI) 216 (M+H)$^+$.

Intermediate 14b

[(1R,2R)-2-(2-Propylbenzoxazol-7-yl)cyclopropyl]formaldehyde

The title compound was prepared by the general procedure described in 14a using 13b (1.32 g), oxalyl chloride (4.3 ml), DMSO (0.89 g), Et$_3$N (2.31 g) to give 1.31 g (100%) of crude product.

$^1$H NMR (300 MHz, CDCl$_3$) δ9.41 (d, J=4.4 Hz, 1H), 7.53 (d, J=7.9 Hz, 1H), 7.21 (t, J=7.7 Hz, 1H). 6.98 (d, J=7.6 Hz, 1H), 2.93–2.84 (m, 3H), 2.48–2.40 (m, 1H), 1.98–1.86 (m, 2H), 1.80 (t, J=7.4 Hz, 2H), 1.06 (t, J=7.4 Hz, 3H).

Intermediate 14c

{(1R,2R)-2-[2-(Methylethyl)benzoxazol-7-yl]cyclopropyl}formaldehyde

The title compound was prepared by the general procedure described in 14a using 13c (1.54 g), oxalyl chloride (5.0 ml), DMSO (1.04 g), Et$_3$N (2.70 g) to give 1.51 g (99%) of crude product.

$^1$H NMR (300 MHz, CDCl$_3$) δ9.41 (d, J=4.5 Hz, 1H), 7.53 (d, J=7.9 Hz, 1H), 7.21 (t, J=7.7 Hz, 1H). 6.98 (d, J=7.6 Hz, 1H), 3.31–3.17 (m, 1H), 2.91–2.84 (m, 1H), 2.48–2.40 (m, 1H), 1.80 (dd, J=8.0, 5.6 Hz, 2H), 1.45 (d, J=7.0 Hz, 3H).

Intermediate 14d

{(1R,2R)-2-[2-(4-Phenylbutyl)benzoxazol-7-yl]cyclopropyl}formaldehyde

The title compound was prepared by the general procedure described in 14a using 13d (1.02 g), oxalyl chloride (2.4 ml), DMSO (0.50 g), Et$_3$N (1.28 g) to give 1.01 g (100%) of crude product.

$^1$H NMR (300 MHz, CDCl$_3$) δ9.42 (d, J=4.4 Hz, 1H), 7.53 (d, J=7.9 Hz, 1H), 7.31–7.16 (m, 6H). 6.99 (d, J=7.7 Hz, 1H), 2.97 (t, J=7.4 Hz, 2H), 2.92–2.84 (m, 1H), 2.70 (t, J=7.5 Hz, 2H), 2.48–2.40 (m, 1H), 2.00–1.89 (m, 2H), 1.84–1.73 (m, 2H), 1.42 (t, J=7.4 Hz, 2H).

Intermediate 15a

[(1R,2R)-2-(2-Ethylbenzoxazol-7-yl)cyclopropyl]methylamine

To a mixture of 14a (800) and NH$_2$OH.HCl (777 mg) in THF (22 mL) was added 1 N NaOH (11.1 mL). The resulting mixture was refluxed for 1 h. After THF was removed, the residue was extracted with EtAcO, washed with brine, dried over MgSO$_4$, and concentrated to give 851 mg (100%) of the desired product that was used in the next step without purification. (IR (film, cm$^{-1}$) 3236; MS(ESI) 231 (M+H)$^+$.) NaBH$_4$ (1.368 g) was added to a solution of the above product (851 mg) and cobalt (II) chloride hexahydrate, CoCl$_2$.6H$_2$O, (3.427 g) at 0° C. After stirring for 1 h, the reaction was quenched with 6 N HCl and MeOH was removed to give a residue. The residue was based with NH₄OH solution, extracted with EtOAc. The organic layer was washed with brine and concentrated to give 600 mg (77%) of the desired product that was used in the next step without purification.

Intermediate 15b

[(1R,2R)-2-(2-Propylbenzoxazol-7-yl)cyclopropyl]methylamine

The title compound was prepared by the general procedure described in 15a using 14b (1.31 g), hydroxylamine hydrochloride (1.19 g), NaOH(1N, 17 ml) to give an oxime intermediate which was treated with sodium borohydride (2.04 g) and cobalt (II) chloride hexahydrate (5.14 g) to afford 1.18 g (89%) of crude amine which was taken to the next step without further purification. MS (ESI): 231 (M+H)⁺.

Intermediate 15c

{(1R,2R)-2-[2-(Methylethyl)benzoxazol-7-yl]cyclopropyl}methylamine

The title compound was prepared by the general procedure described in 15a using 14c (1.46 g), hydroxylamine hydrochloride (1.32 g), NaOH (1N, 20 ml) to give an oxime intermediate which was treated with sodium borohydride (2.06 g) and cobalt (II) chloride hexahydrate (5.18 g) to afford 1.13 g (77%) of crude amine which was taken to the next step without further purification. MS (ESI): 231 (M+H)⁺.

Intermediate 15d

{(1R,2R)-2-[2-(4-Phenylbutyl)benzoxazol-7-yl]cyclopropyl}methylamine

The title compound was prepared by the general procedure described in 15a using 14d (1.01 g), hydroxylamine hydrochloride (0.66 g), NaOH(1N, 10 ml) to give an oxime intermediate which was treated with sodium borohydride (1.01 g) and cobalt (II) chloride hexahydrate (2.53 g) to afford 0.50 g (49%) of crude amine which was taken to the next step without further purification. MS (ESI): 321 (M+H)⁺.

EXAMPLE 1

N-[3-(2-Methyl-7-benzoxazolyl)propyl]acetamide

To a suspension of 5f (115 mg, 0.50 mmol) in 10 mL CH₂Cl₂:THF (1:1) was added Et₃N (150 µL, 1.1 mmol), followed by the addition of an acyl chloride (0.60 mmol). After 1 hour of agitation on a wrist-action shaker, the reaction was rinsed with 1N HCl, and the organic extract was dried with Na₂SO₄. The resulting solution was then passed through SCX solid-phase extraction cartridges using 2.0 g of sorbent, rinsing first with MeOH, and subsequently eluting the desired product with CH₂Cl₂:MeOH:30% aq NH₃ (90:9:1), followed by solvent removal. This compound was obtained as an amber oil (67 mg, 58% yield). HPLC method for LC/MS characterization: start % B=0; final % B=100; gradient time=4 min; flow rate=5 mL/min; detector wavelength 220 nm; solvent A=10% MeOH/90% H₂O/0.1% TFA; solvent B=90% MeOH/10% H₂O/0.1% TFA; column= YMC ODS-A C18 S5 3.0×50 mm. MS (ESI) m/z 233.11 (MH⁺); HPLC purity 89.7%.

EXAMPLE 2

N-[3-(2-Methyl-7-benzoxazolyl)propyl]propanamide

Prepared by the general procedure described for Example 1 above using propionyl chloride. This compound was obtained as an amber oil (77 mg, 63% yield). MS (ESI) m/z 247.11 (MH⁺); HPLC purity 93.7%.

EXAMPLE 3

N-[3-(2-Methyl-7-benzoxazolyl)propyl]butanamide

Prepared by the general procedure described for Example 1 above using butyryl chloride. This compound was obtained as an amber oil (101 mg, 78% yield). MS (ESI) m/z 261.12 (MH⁺); HPLC purity 98.1%.

EXAMPLE 4

N-[3-(2-Methyl-7-benzoxazolyl)propyl]cyclopropanecarboxamide

Prepared by the general procedure described for Example 1 above using cyclopropane carbonyl chloride. This compound was obtained as a white solid (85 mg, 65% yield). MS (ESI) m/z 259.11 (MH⁺); HPLC purity 100%.

EXAMPLE 5

N-[3-(2-Methyl-7-benzoxazolyl)propyl]-2-methylpropanamide

Prepared by the general procedure described for Example 1 above using isobutyryl chloride. This compound was obtained as an amber oil (88 mg, 68% yield). MS (ESI) m/z 261.12 (MH⁺); HPLC purity 97.7%.

EXAMPLE 6

(Ethylamino)-N-[3-(2-methylbenzoxazol-7-yl)propyl]carboxamide

Prepared by the general procedure described for Example 1 above using ethyl isocyanate. This compound was obtained as a light brown oil (21 mg, 50% yield, >95% purity (HPLC)). ¹H NMR (CDCl₃): δ7.48 (d, 1H, J=7.8 Hz), 7.22 (t, 1H, J=7.6 Hz), 7.09 (d, 1H, J=7.8 Hz), 4.39 (br, 1H), 4.26 (br, 1H), 3.21 (m, 4H), 2.91 (t, 2H, J=5.0 Hz), 2.63 (s, 3H), 1.98 (q, 2H, J=8.7 Hz), 1.21 (t, 3H, J=8.7 Hz). MS (ESI): m/z 262.17 (M+H).

EXAMPLE 7

N-[3-(2-Ethylbenzoxazol-7-yl)propyl]acetamide

A solution of acetyl chloride (78 mg) in CH₂Cl₂ was added to a solution of 5a (204 mg) and Et₃N (202 mg) in CH₂Cl₂ (6 mL) at room temperature. After stirring for 16 h, purification by flash chromatography over silica gel (elution with EtOAc) gave 224 mg (91%) of the desired product.

IR (film, cm⁻¹) 3288, 1653; ¹H NMR (300 MHz, CDCl₃): δ7.50 (dd, J=7.8, 0.9 Hz, 1H), 7.25 (t, J=7.6 Hz, 1H), 7.08 (d, J=7.2 Hz, 1H), 5.81 (br s, 1H), 3.32 (q, J=6.8 Hz, 2H), 2.98–2.85 (m, 4H), 1.98–1.88 (m, 5H), 1.46 (t, J=7.5 Hz, 3H); ¹³C NMR (75 MHz,CDCl₃) δ170.3, 168.0, 149.5, 140.9, 124.6, 124.5, 124.3, 39.3, 29.6, 27.4, 23.3, 22.2, 11.0; MS(ESI) 246 (M−1)⁺.

EXAMPLE 8

N-[3-(2-Ethylbenzoxazol-7-yl)propyl]propanamide

The title compound was prepared by the general procedure described in Example 7 using 5a (204 mg), Et₃N (202 mg) and propionyl chloride (93 mg). Purification by flash chromatography over silica gel, elution with 80% EtOAc/hexanes, gave 231 mg (81%) of the desired product.

IR (film, cm$^{-1}$) 3293, 1646; $^1$H NMR (300 MHz, CDCl$_3$): δ7.47 (dd, J=7.8, 0.9 Hz, 1H), 7.18 (t, J=7.6 Hz, 1H), 7.05 (d, J=7.3 Hz, 1H), 5.56 (br s, 1H), 3.41 (q, J=6.9 Hz, 2H), 2.95–2.81 (m, 4H), 2.15 (q, J=7.6 Hz, 2H), 1.94–1.80 (m, 2H), 1.41 (t, J=7.5 Hz, 3H), 1.04 (t, J=7.6 Hz, 3H); $^{13}$C NMR (75 MHz,CDCl$_3$) δ173.8, 168.0, 149.5, 140.7, 124.7, 124.6, 124.4, 39.1, 29.8, 29.7, 27.4, 22.2, 11.0, 10.0; MS(ESI) 259(M−1)$^+$.

EXAMPLE 9

N-[3-(2-Ethylbenzoxazol-7-yl)propyl]butanamide

The title compound was prepared by the general procedure described in Example 7 using 5a (204 mg), Et$_3$N (202 mg) and butyryl chloride (107 mg). Purification by flash chromatography over silica gel (elution with 80% EtOAc/hexanes) gave 252 mg (92%) of the desired product.

IR (film, cm$^{-1}$) 3290, 1645; $^1$H NMR (300 MHz, CDCl$_3$): δ7.51 (dd, J=7.8, 0.9 Hz, 1H), 7.22(t, J=7.6 Hz, 1H), 7.09 (d, J=7.4 Hz, 1H), 5.65 (br s, 1H), 3.33 (q, J=6.8 Hz, 2H), 2.98–2.85 (m, 4H), 2.15 (t, J=7.6 Hz, 2H), 1.94–1.84 (m, 2H), 1.68 (m, 2H), 1.43 (t, J=7.5 Hz, 3H), 0.94 (t, J=7.3 Hz, 3H); $^{13}$C NMR (75 MHz,CDCl$_3$) δ173.1, 168.0, 149.5, 140.7, 124.7, 124.5, 124.3, 39.1, 38.8, 29.8, 27.4, 22.2, 19.2, 13.8, 11.0; MS(ESI) 273 (M−1)$^+$.

EXAMPLE 10

N-[3-(2-Ethylbenzoxazol-7-yl)propyl]-2-methylpropanamide

The title compound was prepared by the general procedure described in Example 7 using 5a (204 mg), Et$_3$N (202 mg) and iso-butyryl chloride (107 mg). Purification by flash chromatography over silica gel (elution with 80% EtOAc/hexanes) gave 252 mg (92%) of the desired product as an oil.

IR (film, cm$^{-1}$) 3290, 1645; $^1$H NMR (300 MHz, CDCl$_3$): δ7.46 (d, J=7.8, Hz, 1H), 7.22(t, J=7.6 Hz, 1H), 7.04 (d, J=7.5 Hz, 1H), 5.58 (br s, 1H), 3.27 (q, J=6.8 Hz, 2H), 2.93–2.80 (m, 4H), 2.29–2.09 (m, 2H), 1.92–1.88 (m, 2H), 1.38 (t, J=7.5 Hz, 3H), 1.07 (d, J=6.9 Hz, 6H); $^{13}$C NMR (75 MHz,CDCl$_3$) δ177.0, 168.0, 149.5, 140.8, 124.7, 124.6, 124.4, 117.3, 39.0, 35.7, 29.8, 27.4, 22.2, 19.7, 11.0; MS(ESI) 273 (M−1)$^+$.

EXAMPLE 11

Cyclopropyl-N-[3-(2-ethylbenzoxazol-7-yl)propyl]carboxamide

The title compound was prepared by the general procedure described in Example 7 using 5a (204 mg), Et$_3$N (202 mg) and cyclopropane carbonyl chloride (105 mg). Purification by flash chromatography over silica gel (elution with 80% EtOAc/hexanes) gave 242 mg (89%) of the desired product as an oil.

IR (film, cm$^{-1}$) 3243, 1636; $^1$H NMR (300 MHz, CDCl$_3$): δ7.56 (dd, J=7.8, 1 Hz, 1H), 7.22 (t, J=7.6 Hz, 1H), 7.14 (d, J=7.5 Hz, 1H), 6.22 (br s, 1H), 3.40 (q, J=6.9 Hz, 2H), 3.01–2.92 (m, 4H), 2.20–1.95 (m, 2H), 1.49 (t, J=7.5 Hz, 3H), 1.40–1.37 (m, 1H), 0.99–0.96 (m, 2H), 0.79–0.71 (m, 2H); $^{13}$C NMR (75 MHz,CDCl$_3$) δ173.1, 167.0, 149.5, 141.0, 124.6, 124.2, 117.9, 39.4, 29.7, 27.4, 22.2, 14.6, 11.0, 7.0; MS(ESI) 271(M−1)$^+$; Anal Calcd for C$_{16}$H$_{20}$N$_2$O$_2$ C, 70.56; H, 7.40; Found: C, 70.22; H, 7.48.

EXAMPLE 12

(Ethylamino)-N-[3-(2-ethylbenzoxazol-7-yl)propyl]carboxamide

A solution of 5a (204 mg) and ethyl isocyanate (142 mg) in benzene (6 mL) was stirred for 16 h. The benzene was removed in vacuo, and the residue was purified by flash chromatography over silica gel, elution with EtOAc to give 233 mg (85%) of the desired product.

IR (film, cm$^{-1}$) 3338, 1626; $^1$H NMR (300 MHz, CDCl$_3$): δ7.46 (dd, J=7.8, 0.9 Hz, 1H), 7.13 (t, J=7.6 Hz, 1H), 7.02 (d, J=6.8 Hz, 1H), 5.26 (br s, 2H), 3.21–3.10 (m, 4H), 2.93–2.81 (m, 4H), 2.93–2.83 (m, 2H), 1.41 (t, J=7.5 Hz, 3H), 1.07 (t, J=7.2 Hz, 3H); $^{13}$C NMR (75 MHz,CDCl$_3$) δ167.9, 158.8, 149.6, 141.4, 124.7, 124.5, 124.2, 117.2, 40.0, 35.2, 30.3, 27.4, 22.2, 15.6, 11.0; MS(ESI) 274 (M−1)$^+$; Anal Calcd for C$_{15}$H$_{21}$N$_3$O$_2$ C, 65.43; H, 7.69; Found: C, 65.3; H, 7.79.

EXAMPLE 13

N-[3-(2-Propylbenzoxazol-7-yl)propyl]acetamide

The title compound was prepared by the general procedure described above in Example 7 using 5b (218 mg), Et$_3$N (202 mg) and acetyl chloride (78 mg). Purification by flash chromatography over silica gel, elution with EtOAc, gave 234 mg (90%) of the desired product.

IR (film, cm$^{-1}$) 3288, 1653; $^1$H NMR (300 MHz, CDCl$_3$): δ7.50 (dd, J=7.9, 1 Hz, 1H), 7.27 (t, J=7.6 Hz, 1H), 7.08 (d, J=6.7 Hz, 1H), 5.89 (br s, 1 H), 3.32 (q, J=6.9 Hz, 2H), 2.91 (t, J=7.4 Hz, 4H), 2.02–1.86 (m, 5H), 1.06 (t, J=7.3 Hz, 3H); $^{13}$C NMR (75 MHz,CDCl$_3$) δ170.4, 167.0, 149.6, 141.2, 124.7, 124.6, 124.1, 117.4, 39.4, 30.7, 29.7, 27.6, 23.4, 20.4, 13.9; MS(ESI) 260 (M−1)$^+$.

EXAMPLE 14

N-[3-(2-Propylbenzoxazol-7-yl)propyl]propanamide

The title compound was prepared by the general procedure described above in Example 7 using 5b (218 mg), Et$_3$N (202 mg) and propionyl chloride (107 mg). Purification by flash chromatography over silica gel, elution with 80% EtOAc/hexanes, gave 252 mg (92%) of the desired product.

IR (film, cm$^{-1}$) 3293, 1646; $^1$H NMR (300 MHz, CDCl$_3$): δ7.51 (dd, J=7.9, 1 Hz, 1H), 7.18 (t, J=7.6 Hz, 1H), 7.05 (d, J=7.3 Hz, 1H), 5.69 (br s, 1H), 3.41 (q, J=5.1 Hz, 2H), 2.925–2.81 (m, 4H), 2.20 (q, J=7.5 Hz, 2H), 1.99–1.80 (m, 4H), 1.15 (t, J=7.6 Hz, 3H), 1.04 (t, J=7.3 Hz, 3H); $^{13}$C NMR (75 MHz,CDCl$_3$) δ174.0, 167.1, 149.6, 141.2, 124.7, 124.6, 124.1, 117.4, 39.2, 30.7, 29.9, 29.8, 27.6, 20.5, 13.9, 10.1; MS(ESI) 273 (M−1)$^+$.

EXAMPLE 15

N-[3-(2-Propylbenzoxazol-7-yl)propyl]butanamide

The title compound was prepared by the general procedure described above in Example 7 using 5b (218 mg), Et$_3$N (202 mg) and butyryl chloride (107 mg). Purification by flash chromatography over silica gel (elution with 50% EtOAc/hexanes) gave 262 mg (88%) of the desired product.

IR (film, cm$^{-1}$) 3291, 1656; $^1$H NMR (300 MHz, CDCl$_3$): δ7.50 (dd, J=7.9, 0.9 Hz, 1H), 7.22 (t, J=7.6 Hz, 1H), 7.09 (d, J=6.9 Hz, 1H), 5.76 (br s, 1H), 3.33 (q, J=6.9 Hz, 2H), 2.91–2.85 (m, 4H), 2.15 (t, J=7.7 Hz, 2H), 2.09–1.81 (m, 4H), 1.68–1.56 (m, 2H), 1.06 (t, J=7.2 Hz, 3H), 0.94 (t, J=7.4

Hz, 3H); $^{13}$C NMR (75 MHz,CDCl$_3$) δ173.2, 167.0, 149.6, 141.2, 124.7, 124.6, 124.1, 117.4, 39.2, 38.9, 30.7, 29.9, 27.6, 20.4, 19.3, 13.9;

MS(ESI) 287 (M−1)$^+$.

EXAMPLE 16

2-Methyl-N-[3-(2-propylbenzoxazol-7-yl)propyl]propanamide

The title compound was prepared by the general procedure described above in Example 7 using 5b (218 mg), Et$_3$N (202 mg) and iso-butyryl chloride (107 mg). Purification by flash chromatography over silica gel (elution with 50% EtOAc/hexanes) gave 244 mg (82%) of the desired product as an oil.

IR (film, cm$^{-1}$) 3296, 1673; $^1$H NMR (300 MHz, CDCl$_3$): δ7.51 (dd, J=7.8, 0.9 Hz, 1H), 7.22(t, J=7.9 Hz, 1H), 7.09 (d, J=7.0 Hz, 1H), 5.68 (br s, 1H), 3.33 (q, J=6.9 Hz, 2H), 2.92–2.84 (m, 4H), 2.35–2.26 (m, 1H), 1.98–1.84 (m, 4H), 1.13 (d, J=6.8 Hz, 6H), 0.95 (t, J=7.1 Hz, 3H); $^{13}$C NMR (75 MHz,CDCl$_3$) δ177.1, 167.0, 149.6, 141.2, 124.7, 124.4, 117.4, 39.1, 35.8, 30.7, 29.9, 27.5, 20.4, 19.8, 13.9; MS(ESI) 287 (M−1)$^+$.

EXAMPLE 17

Cyclopropyl-N-[3-(2-propylbenzoxazol-7-yl)propyl]carboxamide

The title compound was prepared by the general procedure described above in Example 11 using 5b (218 mg), Et$_3$N (202 mg) and cyclopropane carbonyl chloride (105 mg). Purification by flash chromatography over silica gel (elution with 80% EtOAc/hexanes) gave 284 mg (96%) of the desired product.

IR (film, cm$^{-1}$) 3291, 1644; $^1$H NMR (300 MHz, CDCl$_3$): δ7.51 (dd, J=7.9, 1 Hz, 1H), 7.22 (t, J=7.6 Hz, 1H), 7.09 (d, J=6.9 Hz, 1H), 5.96 (br s, 1H), 3.35 (q, J=6.9 Hz, 2H), 2.92 (t, J=7.3 Hz, 4H), 2.03–1.82 (m, 4H), 1.34–1.24 (m, 1H), 1.07 (t, J=7.4 Hz, 3H), 1.40–1.37 (m, 1H), 0.87–0.83 (m, 2H), 0.73–0.63 (m, 2H); $^{13}$C NMR (75 MHz,CDCl$_3$) δ173.1, 167.0, 149.5, 141.0, 124.6, 124.2, 117.9, 39.4, 29.7, 27.4, 22.2, 14.6, 11.0, 7.0; MS(ESI) 285(M−1)$^+$.

EXAMPLE 18

(Ethylamino)-N-[3-(2-propylbenzoxazol-7-yl)propyl]carboxamide

The title compound was prepared by the general procedure described above in Example 12 using 5b (218 mg) and ethyl isocyanate (141 mg). Purification by flash chromatography over silica gel, elution with 80% ethyl acetate, gave 264 mg (90%) of the desired product.

IR (film, cm$^{-1}$) 3331, 1636; $^1$H NMR (300 MHz, CDCl$_3$): δ7.47 (d, J=7.8 Hz, 1H), 7.17 (t, J=7.6 Hz, 1H), 7.04 (d, J=7.3 Hz, 1H), 5.26 (br s, 2H), 3.23–3.10 (m, 4H), 2.88–2.83 (m, 4H), 1.95–1.83 (m, 24H), 1.09 (t, J=7.2 Hz, 3H), 1.00 (t, J=7.4 Hz, 3H); $^{13}$C NMR (75 MHz,CDCl$_3$) δ167.0, 159.0, 149.6, 141.2, 124.8, 124.6, 124.3, 40.1, 35.3, 30.6, 30.5, 27.5, 20.4, 15.7, 13.9; MS(ESI) 288 (M−1)$^+$; Anal Calcd for C$_{16}$H$_{23}$N$_3$O$_2$ C, 66.41; H, 8.01. Found: C, 66.49; H, 8.02.

EXAMPLE 19

N-[3-(2-Phenylbenzoxazol-7-yl)propyl]acetamide

The title compound was prepared by the general procedure described above in Example 7 using 5e (252 mg), Et$_3$N (202 mg) and acetyl chloride (79 mg). Purification by flash chromatography over silica gel (elution with EtOAc) gave 265 mg (90%) of the desired product.

IR (film, cm$^{-1}$) 3291, 1661; $^1$H NMR (300 MHz, CDCl$_3$): δ8.27–8.23 (m, 2H), 7.63 (d, J=7.8 Hz, 1H), 7.54–7.49 (m, 3H), 7.29 (t, J=7.4 Hz, 1H), 7.18 (d, J=6.8 Hz, 1H), 5.83 (br s, 1H), 3.36 (m, 2H), 3.02 (t, J=7.3 Hz, 2H), 2.05–1.97 (m, 5H); $^{13}$C NMR (75 MHz,CDCl$_3$) δ170.4, 162.9, 149.6, 141.9, 131.8, 129.1, 127.7, 127.3, 125.4, 124.9, 118.0, 39.5, 29.7, 27.7, 23.5; MS(ESI) 293 (M−H)$^+$.

EXAMPLE 20

N-[3-(2-Phenylbenzoxazol-7-yl)propyl]propanamide

The title compound was prepared by the general procedure described above in Example 7 using 5e (252 mg), Et$_3$N (202 mg) and propionyl chloride (93 mg). Purification by flash chromatography over silica gel (elution with 30% EtOAc/hexanes) gave 290 mg (94%) of the desired product.

IR (film, cm$^{-1}$) 3295, 1646;

$^1$H NMR (300 MHz, CDCl$_3$): δ8.27–8.23 (m, 2H), 7.63 (dd, J=7.9, 0.9 Hz, 1H), 7.56–7.49 (m, 3H), 7.29 (t, J=7.9 Hz, 1H), 7.14 (d J=7.0 Hz, 1H), 5.73 (br s, 1H), 3.39 (q, J=6.7 Hz, 2H), 3.01 (t, J=7.4 Hz, 2H), 2.26 (q, J=7.6 Hz, 2H), 2.05–1.97 (m, 2H), 1.16 (t, J=7.5 Hz, 3H); $^{13}$C NMR (75 MHz,CDCl$_3$) δ174.7, 162.9, 149.6, 141.9, 131.8, 129.1, 127.7, 127.2, 125.4, 124.9, 118.0, 39.3, 29.9, 29.8, 27.6, 10.1; MS(ESI) 307 (M−H)$^+$.

EXAMPLE 21

N-[3-(2-Phenylbenzoxazol-7-yl)propyl]butanamide

The title compound was prepared by the general procedure described above in Example 7 using 5e (252 mg), Et$_3$N (202 mg) and butyryl chloride (107 mg). Purification by flash chromatography over silica gel (elution with 30% EtOAc/hexanes) gave 287 mg (89%) of the desired product.

IR (film, cm$^{-1}$) 3292, 1644; $^1$H NMR (300 MHz, CDCl$_3$): δ8.29–8.23 (m, 2H), 7.63 (dd, J=7.8, 1 Hz, 1H), 7.56–7.49 (m, 3H), 7.27 (t, J=7.8 Hz, 1H), 7.16 (dt, J=7.0 Hz, 1H), 5.73 (br s, 1H), 3.39 (q, J=6.8 Hz, 2H), 3.02 (t, J=7.5 Hz, 2H), 2.16 (t, J=7.6 Hz, 2H), 2.00–1.97 (m, 2H), 1.71–1.58 (m, 2H), 0.95 (t, J=7.3 Hz, 3H); $^{13}$C NMR (75 MHz,CDCl$_3$) δ173.2, 162.9, 149.6, 141.9, 131.7, 129.1, 127.7, 127.2, 125.4, 124.9, 118.0, 39.3, 38.9, 29.8, 27.6, 19.4, 13.9; MS(ESI) 321 (M−H)$^+$.

EXAMPLE 22

2-Methyl-N-[3-(2-phenylbenzoxazol-7-yl)propyl]propanamide

The title compound was prepared by the general procedure described above in Example 7 using 5e (252 mg), Et$_3$N (202 mg) and iso-butyryl chloride (107 mg). Purification by flash chromatography over silica gel (elution with 30% EtOAc/hexanes) gave 306 mg (96%) of the desired product as an oil.

IR (film, cm$^{-1}$) 3304, 1646; $^1$H NMR (300 MHz, CDCl$_3$): δ8.29–8.23 (m, 2H), 7.63 (dd, J=8, 0.9 Hz, 1H), 7.56–7.49 (m, 3H), 7.27 (t, J=7.5 Hz, 1H), 7.16 (d, J=7.0 Hz, 1H), 5.71 (br s, 1H), 3.38 (q, J=6.8 Hz, 2H), 3.01 (t, J=7.4 Hz, 2H), 2.37–2.28 (m, 1H), 2.06–1.97 (m, 2H), 1.14 (d, J=6.9 Hz, 6H); $^{13}$C NMR (75 MHz,CDCl$_3$) δ177.2, 162.9, 149.6, 141.9, 131.7, 129.1, 127.7, 127.2, 125.4, 125.0, 124.9, 117.9, 39.2, 35.8, 29.9, 27.6, 19.8; MS(ESI) 321 (M−H)$^+$.

EXAMPLE 23

Cyclopropyl-N-[3-(2-phenylbenzoxazol-7-yl)propyl] carboxamide

The title compound was prepared by the general procedure described above in Example 11 using 5e (252 mg), $Et_3N$ (202 mg) and cyclopropane carbonyl chloride (105 mg). Purification by flash chromatography over silica gel (elution with 30% EtOAc/hexanes) gave 282 mg (88%) of the desired product.

IR (film, $cm^{-1}$) 3299, 1643; $^1H$ NMR (300 MHz, $CDCl_3$): δ8.27–8.21(m, 2H), 7.63 (dd, J=7.8, 0.7 Hz, 1H), 7.56–7.49 (m, 3H), 7.28 (t, J=7.6 Hz, 1H), 7.23 (t, J=7.3 Hz, 1H), 5.99 (br s, 1H), 3.40 (q, J=6.8 Hz, 2H), 3.02 (t, J=7.5 Hz, 2H), 2.07–1.97 (m, 2H), 1.35–1.25 (m, 1H), 0.94–0.87 (m, 2H), 0.69–0.61 (m, 2H); $^{13}C$ NMR (75 MHz,$CDCl_3$) δ173.8, 162.9, 149.6, 141.9, 131.7, 129.1, 127.7, 127.3, 125.4, 125.0, 124.9, 117.9, 39.6, 29.8, 27.6, 14.9, 7.2; MS(ESI) 319 $(M-H)^+$.

EXAMPLE 24

(Ethylamino)-N-[3-(2-phenylbenzoxazol-7-yl) propyl]carboxamide

The title compound was prepared by the general procedure described above in Example 12 using 5e (252 mg) and ethyl isocyanate (142 mg). Purification by flash chromatography over silica gel (elution with 80% EtOAc) gave 280 mg (90%) of the desired product.

IR (film, $cm^{-1}$) 3344, 1622; $^1H$ NMR (300 MHz, $CDCl_3$): δ8.26–8.20 (m, 2H), 7.61 (dd, J=7.8, 0.9 Hz, 1H), 7.57–7.48 (m, 3H), 7.27 (t, J=7.7 Hz, 1H), 7.14 (t, J=7.0 Hz, 1H), 4.62 (br s, 2H), 3.39 (t, J=6.9 Hz, 2H), 3.21–3.13 (m, 4H), 3.00 (t, J=7.4 Hz, 2H), 2.05–1.95 (m, 2H), 1.19–1.00 (m, 3H); $^{13}C$ NMR (75 MHz,$CDCl_3$) δ162.9, 158.6, 149.6, 142.0, 131.7, 129.1, 127.7, 127.3, 125.3, 125.1, 124.8, 117.9, 40.2, 35.4, 30.4, 27.6, 15.6; MS(ESI) 322 $(M-H)^+$.

EXAMPLE 25

N-{3-[2-(4-Phenylbutyl)benzoxazol-7-yl] propyl}acetamide

The title compound was prepared by the general procedure described above in Example 7 using 5d (91 mg), $Et_3N$ (101 mg) and Acetyl chloride (32 mg). Purification by flash chromatography over silica gel (elution with EtOAc) gave 91 mg (88%) of the desired product.

IR (film, $cm^{-1}$) 3286, 1650; $^1H$ NMR (300 MHz, $CDCl_3$): δ7.52 (dd, J=7.9, 1 Hz, 1H), 7.30–7.10 (m, 6H), 7.08 (d, J=7.2, 1H), 5.63 (br s, 1H), 3.34 (q, J=6.9 Hz, 2H), 2.96 (t, J=7.3 Hz, 2H), 2.92 (t, J=7.7 Hz, 2H), 2.72(t, J=7.6 Hz, 2H), 2.02–1.72 (m, 9H); $^{13}C$ NMR (75 MHz, $CDCl_3$) δ170.2, 166.9, 149.6, 142.1, 141.3, 128.5, 126.7, 126.0, 124.7, 124.6, 124.0, 117.5, 39.4, 35.6, 31.0, 29.7, 28.7, 27.6, 26.6, 23.5; MS(ESI) 349 $(M-1)^+$.

EXAMPLE 26

N-{3-[2-(4-Phenylbutyl)benzoxazol-7-yl] propyl}propanamide

The title compound was prepared by the general procedure described above in Example 7 using 5d (91 mg), $Et_3N$ (101 mg) and propionyl chloride (37 mg). Purification by flash chromatography over silica gel (elution with 30% EtOAc/hexanes) gave 94 mg (87%) of the desired product.

IR (film, $cm^{-1}$) 3292, 1644; $^1H$ NMR (300 MHz, $CDCl_3$): δ7.53 (dd, J=7.8, 0.9 Hz, 1H), 7.30–7.15 (m, 6H), 7.08 (d, J=7.0 Hz, 1H), 5.54 (br s, 1H), 3.35 (q, J=6.9 Hz, 2H), 2.98 (t, J=7.3 Hz, 2H), 2.92 (t, J=7.7 Hz, 2H), 2.72 (t, J=7.6 Hz, 2H),2.20 (q, J=7.6 Hz, 2H), 1.99–1.72 (m, 6H), 1.16 (t, J=7.6 Hz, 3H); $^{13}C$ NMR (75 MHz,$CDCl_3$) δ173.9, 166.9, 149.6, 142.1, 141.2, 128.5, 126.0, 124.7, 124.6, 124.4, 117.5, 39.2, 35.6, 31.1, 29.9, 29.8, 27.6, 26.6, 10.1; MS(ESI) 363 $(M-1)^+$.

EXAMPLE 27

N-{3-[2-(4-Phenylbutyl)benzoxazol-7-yl] propyl}butanamide

The title compound was prepared by the general procedure described above in Example 7 using 5d (91 mg), $Et_3N$ (101 mg) and butyryl chloride (43 mg). Purification by flash chromatography over silica gel (elution with 50% EtOAc/hexanes) gave 106 mg (93%) of the desired product.

IR (film, $cm^{-1}$) 3290, 1643; $^1H$ NMR (300 MHz, $CDCl_3$): δ7.53 (dd, J=7.8, 0.9 Hz, 1H), 7.30–7.15 (m, 6H), 7.08 (d, J=6.7 Hz, 1H), 5.55 (br s, 1H), 3.35 (q, J=6.9 Hz, 2H), 2.98 (t, J=7.3 Hz, 2H), 2.92 (t, J=7.7 Hz, 2H), 2.72 (t, J=7.5 Hz, 2H),2.17 (t, J=7.6 Hz, 2H), 1.99–1.58 (m, 8H), 1.16 (t, J=7.6 Hz, 3H); $^{13}C$ NMR (75 MHz,$CDCl_3$) δ173.2, 166.9, 149.6, 142.1, 141.2, 128.5, 126.0, 124.7, 124.6, 124.0, 117.5, 39.2, 38.9, 35.6, 31.1, 29.9, 28.7, 27.7, 26.6, 19.3, 13.9; MS(ESI) 377 $(M-1)^+$.

EXAMPLE 28

2-Methyl-N-{3-[2-(4-phenylbutyl)benzoxazol-7-yl] propyl}propanamide

The title compound was prepared by the general procedure described above in Example 7 using 5d (91 mg), $Et_3N$ (101 mg) and iso-butyryl chloride (43 mg). Purification by flash chromatography over silica gel (elution with 50% EtOAc/hexanes) gave 106 mg (95%) of the desired product as an oil.

IR (film, $cm^{-1}$) 3331, 1633; $^1H$ NMR (300 MHz, $CDCl_3$): δ7.53 (dd, J=7.8, 0.9 Hz, 1H), 7.30–7.15 (m, 6H), 7.08 (d, J=7.0 Hz, 1H), 5.57 (br s, 1H), 3.35 (q, J=6.9 Hz, 2H), 2.98 (t, J=7.3 Hz, 2H), 2.92 (t, J=7.7 Hz, 2H), 2.72 (t, J=7.5 Hz, 2H),2.35–2.26 (m, 1H), 1.99–1.72 (m, 6H), 1.16 (t, J=6.9 Hz, 6H); $^{13}C$ NMR (75 MHz,$CDCl_3$) δ177.1, 166.9, 149.6, 142.1, 141.3, 128.5, 126.0, 124.7, 124.4, 117.5, 39.1, 35.8, 35.6, 31.1, 29.9, 28.7, 27.6, 26.6, 19.8, 19.2, 14.3; MS(ESI) 377 $(M-1)^+$.

EXAMPLE 29

Cyclopropyl-N-{3-[2-(4-phenylbutyl)benzoxazol-7-yl]propyl}carboxamide

The title compound was prepared by the general procedure described above in Example 11 using 5d (91 mg), $Et_3N$ (101 mg) and cyclopropane carbonyl chloride (42 mg). Purification by flash chromatography over silica gel (elution with 60% EtOAc/hexanes) gave 89 mg (90%) of the desired product.

IR (film, $cm^{-1}$) 3291, 1643; $^1H$ NMR (300 MHz, $CDCl_3$): δ7.53 (dd, J=7.8, 0.7 Hz, 1H), 7.30–7.15 (m, 6H), 7.08 (d, J=7.1 Hz, 1H), 5.55 (br s, 1H), 3.37 (q, J=6.9 Hz, 2H), 2.98 (t, J=7.3 Hz, 2H), 2.92 (t, J=7.6 Hz, 2H), 2.72 (t, J=7.5 Hz, 2H), 2.00–1.73 (m, 6H), 1.31–1.23 (m, 1H), 1.00–0.88 (m, 2H), 0.73–0.63 (m, 2H); $^{13}C$ NMR (75 MHz,$CDCl_3$) δ173.6, 166.9, 149.7, 142.1, 141.2, 128.5, 126.0, 124.7, 124.4, 117.5, 39.5, 35.6, 31.1, 29.9, 28.7, 27.6, 26.6, 14.9, 7.2; MS(ESI) 375 (M−1)+.

EXAMPLE 30

(Ethylamino)-N-{3-[2-(4-phenylbutyl)benzoxazol-7-yl]propyl}carboxamide

The title compound was prepared by the general procedure described above in Example 12 using 5d (91 mg) and ethyl isocyanate (71 mg). Purification by flash chromatography over silica gel, elution with 80% ethyl acetate, gave 102 mg (91%) of the desired product.

IR (film, cm$^{-1}$) 3295, 1645; $^1$H NMR (300 MHz, CDCl$_3$): δ7.51 (dd, J=7.8, 0.9 Hz, 1H), 7.30–7.10 (m, 6H), 7.08 (m, 1H), 3.25 (q, J=6.9 Hz, 2H), 3.18 (t, J=7.3 Hz, 2H), 2.97–2.83 (m, 4H), 2.71 (t, J=7.6 Hz, 2H), 1.98–1.71 (m, 6H), 1.13 (t, J=7.1 Hz, 3H); $^{13}$C NMR (75 MHz,CDCl$_3$) δ166.9, 158.4, 149.7, 142.1, 141.3, 128.5, 126.0, 124.7, 124.6, 124.0, 117.5, 40.2, 35.6, 35.6, 31.0, 30.4, 28.7, 27.5, 26.6, 15.6; MS(ESI) 378 (M−1)+.

EXAMPLE 31

N-(3-Benzoxazol-7-ylpropyl)acetamide

A solution of 8a (104 mg), CH(OEt)$_3$(1 mL), and PPTS (30 mg) in xylene (10 mL) was refluxed for 1 h. After cooling, purification by flash chromatography over silica gel (elution with EtOAc) gave 69 mg (72%) of the desired compound.

IR (film, cm$^{-1}$) 3293, 1656; $^1$H NMR (300 MHz, CDCl$_3$): δ8.09 (s, 1H), 7.63 (dd, J=7.7, 1.1 Hz, 1H), 7.28 (t, J=7.8 Hz, 1H), 7.19 (d, J=7.1 Hz, 1H), 3.33–3.26 (m, 2H), 2.96 (t, J=7.5 Hz, 2H), 2.03–1.91 (m, 4H); $^{13}$C NMR (75 MHz, CDCl$_3$) δ170.4, 152.4, 148.9, 140.0, 125.8, 125.3, 124.9, 118.5, 39.4, 29.7, 27.6, 23.4; MS(ESI) 317(M−H)+.

EXAMPLE 32

N-(3-Benzoxazol-7-ylpropyl)propanamide

The title compound was prepared by the general procedure described above in Example 31 using 8b (111 mg), CH(OEt)$_3$ (1 mL), and PPTS (30 mg). Purification by flash chromatography over silica gel (elution with EtOAc) gave 72 mg (70%) of the desired compound.

IR (film, cm$^{-1}$) 3295, 1656; $^1$H NMR (300 MHz, CDCl$_3$): δ8.25 (s, 1H), 7.63 (dd, J=6.4, 1.9 Hz, 1H), 7.28 (t, J=7.8 Hz, 1H), 7.19 (d, J=7.1 Hz, 1H), 3.33–3.19 (m, 2H), 2.96 (t, J=7.4 Hz, 2H), 2.24 (q, J=7.6 Hz, 2H), 2.00–1.90 (m, 2H), 1.16 (t, J=7.6 Hz, 3H); $^{13}$C NMR (75 MHz,CDCl$_3$) δ174.1, 152.4, 148.9, 140.0, 125.8, 125.4, 118.5, 39.2, 29.8, 29.6, 27.6, 10.1; MS(ESI) 331(M−H)+.

EXAMPLE 33

N-(3-Benzoxazol-7-ylpropyl)-2-methylpropanamide

The title compound was prepared by the general procedure described above in Example 31 using 8c (1181 mg), CH(OEt)$_3$ (1 mL), and PPTS (35 mg). Purification by flash chromatography over silica gel (elution with EtOAc) gave 75 mg (69%) of the desired compound.

IR (film, cm$^{-1}$) 3296, 1645; $^1$H NMR (300 MHz, CDCl$_3$): δ8.25 (s, 1H), 7.63 (dd, J=7.9, 1.0 Hz, 1H), 7.28 (t, J=7.6 Hz, 1H), 7.19 (d, J=7.4 Hz, 1H), 3.33–3.19 (m, 2H), 2.96 (t, J=7.5 Hz, 2H), 2.36–2.27 (m, 1H), 2.00–1.90 (m, 2H), 1.16 (t, J=6.9 Hz, 6H); $^{13}$C NMR (75 MHz,CDCl$_3$) δ177.2, 152.4, 148.9, 140.0, 125.8, 125.4, 124.9, 118.5, 39.1, 35.8, 29.8, 27.8, 19.8; MS(ESI) 345(M−H)+.

EXAMPLE 34

N-{3-[2-(Methylethyl)benzoxazol-7-yl]propyl}acetamide

The title compound was prepared by the general procedure described above in Example 7 using 5c (218 mg), Et$_3$N (202 mg) and acetyl chloride (79 mg). Purification by flash chromatography over silica gel, elution with 50% EtOAc/hexanes, gave 222 mg (85%) of desired product.

$^1$H NMR (300 MHz, CDCl$_3$) δ7.51 (d, J=7.9 Hz, 1H), 7.20 (t, J=7.7 Hz, 1H), 7.08 (d, J=7.4 Hz, 1H), 5.77 (br, s, 1H), 3.34–3.16 (m, 3H), 2.90 (t, J=7.5 Hz, 2H), 2.00–1.90 (m, 2H), 1.95 (s, 3H), 1.45 (d, J=7.0 Hz, 6H); $^{13}$C NMR (75 MHz, CDCl$_3$) δ171.0, 170.0, 149.4, 140.9, 124.4, 124.3, 124.1, 117.4, 39.2, 29.5, 28.8, 27.3, 23.2, 20.3; MS (ESI): 261 (M+H)+.

EXAMPLE 35

N-{3-[2-(Methylethyl)benzoxazol-7-yl]propyl}propanamide

The title compound was prepared by the general procedure described above in Example 7 using 5c (218 mg), Et$_3$N (202 mg) and propionyl chloride (93 mg). Purification by flash chromatography over silica gel, elution with 30% EtOAc/hexanes, gave 206 mg (75%) of desired product.

$^1$H NMR (300 MHz, CDCl$_3$) δ7.46(d, J=7.9 Hz, 1H), 7.15 (t, J=7.7 Hz, 1H), 7.03 (d, J=7.5 Hz, 1H), 6.02 (br, s, 1H), 3.31–3.13 (m, 3H), 2.86 (t, J=7.6 Hz, 2H), 2.14 (q, J=7.6 Hz, 2H), 1.96–1.86 (m, 2H), 1.41 (d, J=6.9 Hz, 6H), 1.08 (t, J=7.6 Hz, 3H); $^{13}$C NMR (75 MHz, CDCl$_3$) δ173.7, 170.8, 149.3, 140.8, 124.4, 124.3, 124.0, 117.2, 38.9, 29.5, 29.4, 28.7, 27.2, 20.1, 9.7; MS (ESI): 275 (M+H)+.

EXAMPLE 36

N-{3-[2-(Methylethyl)benzoxazol-7-yl]propyl}butanamide

The title compound was prepared by the general procedure described above in Example 7 using 5c (218 mg), Et$_3$N (202 mg) and butyryl chloride (107 mg). Purification by flash chromatography over silica gel, elution with 30% EtOAc/hexanes, gave 245 mg (85%) of desired product.

$^1$H NMR (300 MHz, CDCl$_3$) δ7.54 (d, J=7.8 Hz, 1H), 7.26 (t, J=7.8 Hz, 1H), 7.11 (d, J=7.5 Hz, 1H), 5.57 (br, s, 1H), 3.37–3.23 (m, 3H), 2.92 (t, J=7.6 Hz, 2H), 2.13 (t, J=7.4 Hz, 2H), 1.99–1.92 (m, 2H), 1.71–1.59 (m, 2H), 1.48 (d, J=6.9 Hz, 6H), 0.94 (t, J=7.4 Hz, 3H); $^{13}$C NMR (75 MHz, CDCl$_3$) δ173.0, 171.1, 149.4, 140.5, 124.7, 124.4, 117.2, 39.1, 38.8, 29.7, 28.9, 27.4, 20.4, 19.2, 13.7; MS (ESI): 289 (M+H)+.

EXAMPLE 37

2-Methyl-N-{3-[2-(methylethyl)benzoxazol-7-yl]propyl}propanamide

The title compound was prepared by the general procedure described above in Example 7 using 5c (218 mg), Et$_3$N (202 mg) and iso-butyryl chloride (107 mg). Purification by flash chromatography over silica gel, elution with 30% EtOAc/hexanes, gave 247 mg (86%) of desired product.

$^1$H NMR (300 MHz, CDCl$_3$) δ7.51 (d, J=7.9 Hz, 1H), 7.22 (t, J=7.7 Hz, 1H), 7.08 (d, J=7.4 Hz, 1H), 5.70 (br, s,

1H), 3.34–3.18 (m, 3H), 2.89 (t, J=7.5 Hz, 2H), 2.39–2.24 (m, 1H), 1.99–1.89 (m, 2H), 1.45 (d, J=6.9 Hz, 6H), 1.11 (d, J=6.9 Hz, 6H); $^{13}$C NMR (75 MHz, CDCl$_3$) δ176.9, 171.0, 149.4, 140.9, 124.4, 124.1, 117.3, 38.9, 35.6, 29.6, 28.8, 27.3, 20.3, 19.5; MS (ESI): 289 (M+H)$^+$.

EXAMPLE 38

Cyclopropyl-N-{3-[2-(methylethyl)benzoxazol-7-yl]propyl}carboxamide

The title compound was prepared by the general procedure described above in Example 11 using 5c (218 mg), Et$_3$N (202 mg) and cyclopropane carbonyl chloride (105 mg). Purification by flash chromatography over silica gel, elution with 30% EtOAc/hexanes, gave 245 mg (86%) of desired product.

$^1$H NMR (300 MHz, CDCl$_3$) δ7.51 (d, J=7.8 Hz, 1H), 7.20 (t, J=7.6 Hz, 1H), 7.09 (d, J=7.4 Hz, 1H), 5.91 (br, s, 1H), 3.36–3.19 (m, 3H), 2.91 (t, J=7.4 Hz, 2H), 2.01–1.91 (m, 2H),1.45 (d, J=6.9 Hz, 6H), 1.34–1.25 (m, 1H), 0.96–0.91 (m, 2H), 0.72–0.66 (m, 2H); $^{13}$C NMR (75 MHz, CDCl$_3$) δ173.4, 171.0, 149.4, 140.9, 124.5, 124.4, 124.1, 117.3, 39.3, 29.6, 28.8, 27.3, 20.3, 14.6, 6.9; MS (ESI): 287 (M+H)$^+$.

EXAMPLE 39

(Ethylamino)-N-{3-[2-(methylethyl)benzoxazol-7-yl]propyl}carboxamide

The title compound was prepared by the general procedure described above in Example 12 using 5c (218 mg), ethyl isocyanate (142 mg). Purification by flash chromatography over silica gel, elution with 50% EtOAc/hexanes, gave 244 mg (84%) of desired product.

$^1$H NMR (300 MHz, CDCl$_3$) δ7.49 (d, J=7.8 Hz, 1H), 7.16 (t, J=7.6 Hz, 1H), 7.05 (d, J=7.5 Hz, 1H), 5.07 (br, s, 2H), 3.25–3.12 (m, 5H), 2.88 (t, J=7.5 Hz, 2H), 1.96–1.87 (m, 2H),1.43 (d, J=6.9 Hz, 6H), 1.08 (t, J=7.2 Hz, 3H); $^{13}$C NMR (75 MHz, CDCl$_3$) δ171.0, 158.6, 149.4, 141.0, 124.6, 124.4, 124.0, 117.2, 39.9, 35.1, 30.2, 28.8, 27.3, 20.3, 15.4; MS (ESI): 290 (M+H)$^+$.

EXAMPLE 40

(t-Butoxy)-N-[3-(6-bromo-2-ethylbenzoxazol-7-yl)propyl]carboxamide

A suspension of N-t-butoxycarbonyl 4-bromo-2-propionamido-6-(3-aminopropyl)phenol (1.47 g, 3.7 mmol) and pyridinium p-toluenesulfonate (0.23 g, 0.92 mmol) in xylenes (40 mL) was refluxed for 16 hours. The crude reaction mixture was poured directly on a silica gel column, and the product was eluted with 20% EtOAc/hexanes to obtain the product as an oil which very slowly crystallized (831 mg, 59%).

HPLC (C-18 column, 3.0×50 mm, % B 0–100, 2 min gradient, 5 mL/min) 1.85 min; $^1$H-NMR δ(CDCl$_3$) 1.45 (9H, s), 1.45 (3H, t, J=8 Hz), 1.91 (2H, p, J=7 Hz), 2.86 (2H, t J=8 Hz), 2.96 (2H, q, J=8 Hz), 3.19 (2H, brq, J=6 Hz), 4.61 (1H, brs), 7.23 (1H, d, J=2 Hz), 7.64 (1H, d, J=2 Hz); MS (ESI): 405.1 (M+Na)$^+$.

EXAMPLE 41

N-t-Butoxycarbonyl 7-(3-aminopropyl)-6-vinyl-2-ethylbenzoxazole

A solution of N-t-butoxycarbonyl 7-(3-aminopropyl)-6-bromo-2-ethylbenzoxazole (396 mg, 1.03 mmol), vinyl-tributyltin (360 mg, 1.14 mmol), and tetrakis (triphenylphosphine)palladium (0) (60 mg, 0.052 mmol) in toluene (10 mL) was refluxed for 3 hours. The crude reaction mixture was poured directly on a silica gel column, and the tin by-products were eluted with hexanes. The product was eluted with 25% EtOAc/hexanes to give a clear oil (180 mg, 53%).

HPLC (C-18 column, 3.0×50 mm, % B 0–100, 2 min gradient, 5 mL/min) 1.92 min; $^1$H-NMR δ(CDCl$_3$) 1.45 (9H, s), 1.45 (3H, buried), 1.84 (2H, p, J=8 Hz), 2.90–3.02 (4H, m), 3.15 (2H, brq, J=7 Hz), 4.65 (1H, brs), 5.34 (1H, dd, J=11, 1 Hz), 5.70 (1H, dd, J=17, 1 Hz), 7.00 (1H, dd, J=17, 11 Hz), 7.48 (2H, s); MS (ESI): 331.0 (M+H)$^+$.

EXAMPLE 42

N-Acetyl-7-(3-aminopropyl)-6-bromo-2-ethylbenzoxazole

A solution of N-t-butoxycarbonyl 7-(3-aminopropyl)-6-bromo-2-ethylbenzoxazole (30 mg, 0.078 mmol), in methylene chloride (1 mL) was treated with 4 M HCl in dioxane (1 mL) and stirred for 2 hours. The solvent was evaporated and the residue was taken up in pyridine (2 mL) and treated with acetic anhydride (100 μL). After stirring for 2 hours, the reaction was diluted with EtOAc (5 mL) and washed with saturated aqueous copper (II) sulfate (2×5 mL). The organic layer was dried with magnesium sulfate and evaporated. The product was purified on a silica gel column and eluted with 25% EtOAc/hexanes to give a clear oil (10 mg, 40%).

HPLC (C-18 column, 3.0×50 mm, % B 0–100, 2 min gradient, 5 mL/min) 1.67 min; $^1$H-NMR δ(CDCl$_3$) 1.45 (3H, t, J=8 Hz), 1.91 (2H, p, J=8 Hz), 1.98 (3H, s), 2.95 (2H, q, J=8 Hz), 3.03 (2H, t, J=7 Hz), 3.34 (2H, q, J=7 Hz), 5.60 (1H, brs), 7.37 (1H, d, J=8 Hz), 7.47 (1H, d, J=8 Hz); MS (ESI): 324.9 (M+H)$^+$.

EXAMPLE 43

N-Acetyl-7-(3-aminopropyl)-6-vinyl-2-ethylbenzoxazole

A solution of N-t-butoxycarbonyl 7-(3-aminopropyl)-6-vinyl-2-ethylbenzoxazole (30 mg, 0.091 mmol), in methylene chloride (1 mL) was treated with 4 M HCl in dioxane (1 mL) and stirred for 2 hours. The solvent was evaporated and the residue was taken up in pyridine (2 mL) and treated with acetic anhydride (100 μL). After stirring for 2 hours, the reaction was diluted with EtOAc (5 mL) and washed with saturated aqueous copper (II) sulfate (2×5 mL). The organic layer was dried with magnesium sulfate and evaporated. The product was purified on a silica gel column and eluted with 25% EtOAc/hexanes to give a clear oil (16 mg, 64%).

HPLC (C-18 column, 3.0×50 mm, % B 0–100, 2 min gradient, 5 mL/min) 1.51 min; $^1$H-NMR δ(CDCl$_3$) 1.45 (3H, t, J=8 Hz), 1.85 (2H, p, J=8 Hz), 1.95 (3H, s), 2.90–3.02 (4H, m), 3.27 (2H, q, J=6 Hz), 5.34 (1H, dd, J=11, 1 Hz), 5.62 (1H, brs), 5.69 (1H, dd, J=17, 1 Hz), 6.99 (1H, dd, J=17, 11 Hz), 7.47 (2H, s); MS (ESI): 273.0 (M+H)$^+$.

EXAMPLE 44

N-[3-(2-Ethyl-6-methylbenzoxazol-7-yl)propyl]acetamide

A solution of N-t-butoxycarbonyl protected amine (up to 0.15 mmol) in methylene chloride (2 mL) was treated with 4M HCl in dioxane (2 mL) and shaken for 4 hours. The solvent was then evaporated. The product was dissolved in methanol (1 mL) and divided into 3 separate vials, and the contents of each vial were evaporated to dryness and left under high vacuum for 16 hours. Corresponding acid chloride solutions (0.05 mmol in methylene chloride) were prepared from acetyl chloride, benzoyl chloride, and cyclopropanecarbonyl chloride. To the three vials for the starting amine was added 2 mL of an acid chloride solution. Polyvinyl pyridine resin (100 mg) was then added to each vial, and the vials were capped and shaken for 48 hours. To each vial was then added WA-21J resin (100 mg) and the vials were again shaken for 4 hours. The contents of each vial were filtered and evaporated.

HPLC (C-18 column, 3.0×50 mm, % B 0–100, 2 min gradient, 5 mL/min) 1.42 min; MS (ESI): 283.3 (M+Na)$^+$.

EXAMPLE 45

N-[3-(2-Ethyl-6-methylbenzoxazol-7-yl)propyl] benzamide

Prepared as described above for Example 44.

HPLC (C-18 column, 3.0×50 mm, % B 0–100, 2 min gradient, 5 mL/min) 1.65 min; MS (ESI): 323.3 (M+H)$^+$.

EXAMPLE 46

Cyclopropyl-N-[3-(2-ethyl-6-methylbenzoxazol-7-yl)propyl]carboxamide

Prepared as described above for Example 44.

HPLC (C-18 column, 3.0×50 mm, % B 0–100, 2 min gradient, 5 mL/min) 1.52 min; MS (ESI): 287.2 (M+H)$^+$.

EXAMPLE 47

N-{3-[2-Ethyl-6-(4-fluorophenyl)benzoxazol-7-yl]propyl}acetamide

Prepared as described above for Example 44.

HPLC (C-18 column, 3.0×50 mm, % B 0–100, 2 min gradient, 5 mL/min) 1.55 min; MS (ESI): 341.2 (M+H)$^+$.

EXAMPLE 48

N-{3-[2-Ethyl-6-(4-fluorophenyl)benzoxazol-7-yl]propyl}benzamide

Prepared as described above for Example 44.

HPLC (C-18 column, 3.0×50 mm, % B 0–100, 2 min gradient, 5 mL/min) 1.70 min; MS (ESI): 403.2 (M+H)$^+$.

EXAMPLE 49

Cyclopropyl-N-{3-[2-ethyl-6-(4-fluorophenyl) benzoxazol-7-yl]propyl}carboxamide

Prepared as described above for Example 44.

HPLC (C-18 column, 3.0×50 mm, % B 0–100, 2 min gradient, 5 mL/min) 1.61 min; Mass Spec. (ESI): 367.2 (M+H)$^+$.

EXAMPLE 50

N-(3-{2-Ethyl-6-[4-(trifluoromethyl)phenyl] benzoxazol-7-yl}propyl)acetamide

Prepared as described above for Example 44.

HPLC (C-18 column, 3.0×50 mm, % B 0–100, 2 min gradient, 5 mL/min) 1.68 min; Mass Spec. (ESI): 391.2 (M+H)$^+$.

EXAMPLE 51

Cyclopropyl-N-(3-{2-ethyl-6-[4-(trifluoromethyl) phenyl]benzoxazol-7-yl}propyl)carboxamide Prepared as described above for Example 44.

HPLC (C-18 column, 3.0×50 mm, % B 0–100, 2 min gradient, 5 mL/min) 1.75 min; Mass Spec. (ESI): 417.2 (M+H)$^+$.

EXAMPLE 52

N-{3-[2-Ethyl-6-(4-methoxyphenyl)benzoxazol-7-yl]propyl}acetamide

Prepared as described above for Example 44.

HPLC (C-18 column, 3.0×50 mm, % B 0–100, 2 min gradient, 5 mL/min) 1.53 min; Mass Spec. (ESI): 353.2 (M+H)$^+$.

EXAMPLE 53

N-{3-[2-Ethyl-6-(4-methoxyphenyl)benzoxazol-7-yl]propyl}benzamide

Prepared as described above for Example 44.

HPLC (C-18 column, 3.0×50 mm, % B 0–100, 2 min gradient, 5 mL/min) 1.69 min; Mass Spec. (ESI): 415.2 (M+H)$^+$.

EXAMPLE 54

Cyclopropyl-N-{3-[2-ethyl-6-(4-methoxyphenyl) benzoxazol-7-yl]propyl}carboxamide Prepared as described above for Example 44.

HPLC (C-18 column, 3.0×50 mm, % B 0–100, 2 min gradient, 5 mL/min) 1.61 min; Mass Spec. (ESI): 379.2 (M+H)$^+$.

EXAMPLE 55

N-[3-(2-Ethyl-6-phenylbenzoxazol-7-yl)propyl] acetamide

Prepared as described above for Example 44.

HPLC (C-18 column, 3.0×50 mm, % B 0–100, 2 min gradient, 5 mL/min) 1.52 min; Mass Spec. (ESI): 323.2 (M+H)$^+$.

EXAMPLE 56

N-[3-(2-Ethyl-6-phenylbenzoxazol-7-yl)propyl] benzamide

Prepared as described above for Example 44.

HPLC (C-18 column, 3.0×50 mm, % B 0–100, 2 min gradient, 5 mL/min) 1.70 min; Mass Spec. (ESI): 385.2 (M+H)$^+$.

EXAMPLE 57

Cyclopropyl-N-[3-(2-ethyl-6-phenylbenzoxazol-7-yl)propyl]carboxamide

Prepared as described above for Example 44.

HPLC (C-18 column, 3.0×50 mm, % B 0–100, 2 min gradient, 5 mL/min) 1.60 min; Mass Spec. (ESI): 349.2 (M+H)$^+$.

EXAMPLE 58

N-[3-(2-Ethyl-5-(4-fluorophenyl)benzoxazol-7-yl)propyl]acetamide

Prepared as described above for Example 44.

HPLC (C-18 column, 3.0×50 mm, % B 0–100, 2 min gradient, 5 mL/min) 1.59 min; Mass Spec. (ESI): 341.2 (M+H)$^+$.

EXAMPLE 59

N-{3-[2-Ethyl-5-(4-fluorophenyl)benzoxazol-7-yl]propyl}benzamide

Prepared as described above for Example 44.

HPLC (C-18 column, 3.0×50 mm, % B 0–100, 2 min gradient, 5 mL/min) 1.75 min; Mass Spec. (ESI): 403.2 (M+H)$^+$.

EXAMPLE 60

Cyclopropyl-N-{3-[2-ethyl-5-(4-fluorophenyl)benzoxazol-7-yl]propyl}carboxamide

Prepared as described above for Example 44.

HPLC (C-18 column, 3.0×50 mm, % B 0–100, 2 min gradient, 5 mL/min) 1.67 min; Mass Spec. (ESI): 367.2 (M+H)$^+$.

EXAMPLE 61

N-(3-{2-Ethyl-5-[4-(trifluoromethyl)phenyl]benzoxazol-7-yl}propyl)benzamide

Prepared as described above for Example 44.

HPLC (C-18 column, 3.0×50 mm, % B 0–100, 2 min gradient, 5 mL/min) 1.87 min; Mass Spec. (ESI): 453.2 (M+H)$^+$.

EXAMPLE 62

N-{3-[2-Ethyl-5-(4-methoxyphenyl)benzoxazol-7-yl]propyl}acetamide

Prepared as described above for Example 44.

HPLC (C-18 column, 3.0×50 mm, % B 0–100, 2 min gradient, 5 mL/min) 1.57 min; Mass Spec. (ESI): 353.2 (M+H)$^+$.

EXAMPLE 63

N-{3-[2-Ethyl-5-(4-methoxyphenyl)benzoxazol-7-yl]propyl}benzamide

Prepared as described above for Example 44.

HPLC (C-18 column, 3.0×50 mm, % B 0–100, 2 min gradient, 5 mL/min) 1.73 min; Mass Spec. (ESI): 415.2 (M+H)$^+$.

EXAMPLE 64

Cyclopropyl-N-{3-[2-ethyl-5-(4-methoxyphenyl)benzoxazol-7-yl]propyl}carboxamide

Prepared as described above for Example 44.

HPLC (C-18 column, 3.0×50 mm, % B 0–100, 2 min gradient, 5 mL/min) 1.63 min; Mass Spec. (ESI): 379.3 (M+H)$^+$.

EXAMPLE 65

N-[3-(2-Ethyl-5-phenylbenzoxazol-7-yl)propyl]acetamide

Prepared as described above for Example 44.

HPLC (C-18 column, 3.0×50 mm, % B 0–100, 2 min gradient, 5 mL/min) 1.56 min; Mass Spec. (ESI): 323.2 (M+H)$^+$.

EXAMPLE 66

N-[3-(2-Ethyl-5-phenyl benzoxazol-7-yl)propyl]benzamide

Prepared as described above for Example 44.

HPLC (C-18 column, 3.0×50 mm, % B 0–100, 2 min gradient, 5 mL/min) 1.73 min; Mass Spec. (ESI): 385.2 (M+H)$^+$.

EXAMPLE 67

Cyclopropyl-N-[3-(2-ethyl-5-phenylbenzoxazol-7-yl)propyl]carboxamide

Prepared as described above for Example 44.

HPLC (C-18 column, 3.0×50 mm, % B 0–100, 2 min gradient, 5 mL/min) 1.64 min; Mass Spec. (ESI): 349.2 (M+H)$^+$.

EXAMPLE 68

N-[3-(5-Bromo-2-ethylbenzoxazol-7-yl)propyl]acetamide

Prepared as described above for Example 44.

HPLC (C-18 column, 3.0×50 mm, % B 0–100, 2 min gradient, 5 mL/min) 1.39 min; Mass Spec. (ESI): 325.0 (M+H)$^+$.

EXAMPLE 69

N-[3-(5-Bromo-2-ethylbenzoxazol-7-yl)propyl]benzamide

Prepared as described above for Example 44.

HPLC (C-18 column, 3.0×50 mm, % B 0–100, 2 min gradient, 5 mL/min) 1.60 min; Mass Spec. (ESI): 387.1 (M+H)$^+$.

EXAMPLE 70

N-[3-(5-Bromo-2-ethylbenzoxazol-7-yl)propyl]cyclopropylcarboxamide

Prepared as described above for Example 44.

HPLC (C-18 column, 3.0×50 mm, % B 0–100, 2 min gradient, 5 mL/min) 1.49 min; Mass Spec. (ESI): 351.1 (M+H)$^+$.

EXAMPLE 71

N-[3-(2-Ethyl-5-vinylbenzoxazol-7-yl)propyl]benzamide

Prepared as described above for Example 44.

HPLC (C-18 column, 3.0×50 mm, % B 0–100, 2 min gradient, 5 mL/min) 1.58 min; Mass Spec. (ESI): 335.1 (M+H)$^+$.

EXAMPLE 72

Cyclopropyl-N-[3-(2-ethyl-5-vinylbenzoxazol-7-yl)propyl]carboxamide

Prepared as described above for Example 44.

HPLC (C-18 column, 3.0×50 mm, % B 0–100, 2 min gradient, 5 mL/min) 1.45 min; Mass Spec. (ESI): 299.2 (M+H)$^+$.

EXAMPLE 73

N-[3-(2-Ethyl-6-(2-furyl)benzoxazol-7-yl)propyl]acetamide

Prepared as described above for Example 44.

HPLC (C-18 column, 3.0×50 mm, % B 0–100, 2 min gradient, 5 mL/min) 1.48 min; Mass Spec. (ESI): 313.3 (M+H)$^+$.

EXAMPLE 74

N-[3-(2-Ethyl-6-(2-furyl)benzoxazol-7-yl)propyl]benzamide

Prepared as described above for Example 44.

HPLC (C-18 column, 3.0×50 mm, % B 0–100, 2 min gradient, 5 mL/min) 1.66 min; Mass Spec. (ESI): 375.2 (M+H)$^+$.

EXAMPLE 75

Cyclopropyl-N-[3-(2-ethyl-6-(2-furyl)benzoxazol-7-yl)propyl]carboxamide

Prepared as described above for Example 44.

HPLC (C-18 column, 3.0×50 mm, % B 0–100, 2 min gradient, 5 mL/min) 1.55 min; Mass Spec. (ESI): 339.2 (M+H)$^+$.

EXAMPLE 76

N-{[(1R,2R)-2-(2-Ethylbenzoxazol-7-yl)cyclopropyl]methyl}acetamide

The title compound was prepared by the general procedure described above in Example 7 using 15a (86 mg), Et$_3$N (101 mg) and acetyl chloride (32 mg). Purification by flash chromatography over silica gel (elution with EtOAc) gave 265 mg (90%) of the desired product.

IR (film, cm$^{-1}$) 3291, 1656; $^1$H NMR (300 MHz, CDCl$_3$): δ7.43 (dd, J=7.9, 1.0 Hz, 1H), 7.16 (t, J=7.8 Hz, 1H), 6.85 (d, J=7.3 Hz, 1H), 6.30 (br s, 1H), 3.49–3.40 (m, 1H), 3.21–3.12 (m, 1H), 2.89 (q, J=7.5 Hz, 2H), 2.16–1.99 (m, 1H), 1.92 (s, 3H), 1.57–1.43 (m, 1H), 1.41 (t, J=7.5 Hz, 3H), 1.25–1.11 (m, 1H), 1.01–0.83 (m, 1H); $^{13}$C NMR (75 MHz,CDCl$_3$) δ170.4, 167.9, 149.5, 141.1, 125.9, 124.3, 121.4, 116.8, 49.9, 23.4, 21.7, 21.4, 17.3, 13.5, 11.1; MS(ESI) 257(M–H)$^+$.

EXAMPLE 77

N-{[(1R,2R)-2-(2-Ethylbenzoxazol-7-yl)cyclopropyl]methyl}propanamide

The title compound was prepared by the general procedure described above in Example 7 using 15a (86 mg), Et$_3$N (101 mg) and propionyl chloride (37 mg). Purification by flash chromatography over silica gel (elution with 30% EtOAc/hexanes) gave 290 mg (94%) of the desired product.

IR (film, cm$^{-1}$) 3284, 1656; $^1$H NMR (300 MHz, CDCl$_3$): δ7.50 (dd, J=7.8, 1.0 Hz, 1H), 7.19 (t, J=7.8 Hz, 1H), 6.89 (d, J=7.4 Hz, 1H), 5.89 (br s, 1H), 3.52–3.43 (m, 1H), 3.29–3.17 (m, 1H), 2.91 (q, J=7.5 Hz, 2H), 2.26 (q, J=7.3 Hz, 2H), 2.16–2.00 (m, 1H), 1.58–1.42 (m, 4H), 1.23–0.99 (m, 5H); $^{13}$C NMR (75 MHz,CDCl$_3$) δ173.9, 168.0, 149.6, 141.2, 125.9, 124.3, 121.4, 116.9, 43.8, 29.9, 22.3, 21.5, 17.3, 13.4, 11.1, 10.1; MS(ESI) 271 (M–H)$^+$.

EXAMPLE 78

N-{[(1R,2R)-2-(2-Ethylbenzoxazol-7-yl)cyclopropyl]methyl}butanamide

The title compound was prepared by the general procedure described in Example 7, using 15a (86 mg), Et$_3$N (101 mg) and butyryl chloride (43 mg). Purification by flash chromatography over silica gel (elution with 30% EtOAc/hexanes) gave 287 mg (89%) of the desired product.

IR (film, cm$^{-1}$) 3291, 1645; $^1$H NMR (300 MHz, CDCl$_3$): δ7.47 (dd, J=7.8, 1.0 Hz, 1H), 7.17 (t, J=7.7 Hz, 1H), 6.87 (d, J=7.3 Hz, 1H), 5.98 (br s, 1H), 3.52–3.43 (m, 1H), 3.29–3.17 (m, 1H), 2.97 (q, J=7.5 Hz, 2H), 2.29 (t, J=7.3 Hz, 2H), 2.16–2.03 (m, 1H), 1.72–1.41 (m, 6H), 1.22–1.16 (m, 1H), 1.16–1.03 (m, 4H); $^{13}$C NMR (75 MHz,CDCl$_3$) δ173.2, 168.0, 149.6, 141.1, 125.9, 124.3, 121.4, 116.9, 43.7, 38.8, 22.3, 21.5, 19.3, 17.3, 13.9, 13.4, 11.1; MS(ESI) 285(M–H)$^+$.

EXAMPLE 79

N-{[(1R,2R)-2-(2-Ethylbenzoxazol-7-yl)cyclopropyl]methyl}-2-methylpropanamide

The title compound was prepared by the general procedure described in Example 7, using 15a (86 mg), Et$_3$N (101 mg) and iso-butyryl chloride (43 mg). Purification by flash chromatography over silica gel (elution with 30% EtOAc/hexanes) gave 306 mg (96%) of the desired product as an oil.

IR (film, cm$^{-1}$) 3291, 1656; $^1$H NMR (300 MHz, CDCl$_3$): δ7.51 (dd, J=8.0, 1.0 Hz, 1H), 7.17 (t, J=7.7 Hz, 1H), 6.89 (d, J=7.4 Hz, 1H), 5.98 (br s, 1H), 3.52–3.43 (m, 1H), 3.23–3.17 (m, 1H), 2.97 (q, J=7.4 Hz, 2H), 2.41–2.32 (m, 1H), 12.15–2.05 (m, 1H), 1.57–1.40 (m, 4H), 1.22–0.96 (m, 8H); $^{13}$C NMR (75 MHz,CDCl$_3$) δ177.1, 168.0, 149.6, 141.2, 125.9, 124.3, 121.5, 43.6, 35.8, 22.3, 21.5, 19.9, 19.8, 17.2, 13.3, 11.1 IR (film, cm$^{-1}$) 3291, 1645; MS(ESI) 285(M–H)$^+$.

EXAMPLE 80

N-{[(1R,2R)-2-(2-Ethylbenzoxazol-7-yl)cyclopropyl]methyl}cyclopropylcarboxamide

The title compound was prepared by the general procedure described in Example 7, using 15a (86 mg), Et$_3$N (101 mg) and cyclopropane carbonyl chloride (42 mg). Purification by flash chromatography over silica gel (elution with 30% EtOAc/hexanes) gave 282 mg (88%) of the desired product.

IIR (film, cm$^{-1}$) 3291, 1655; $^1$H NMR (300 MHz, CDCl$_3$): δ7.49 (dd, J=7.4, 1.0 Hz, 1H), 7.17 (t, J=7.7 Hz, 1H), 6.87 (d, J=7.3 Hz, 1H), 6.29 (br s, 1H), 3.52–3.43 (m, 1H); 3.29–3.17 (m, 1H), 2.97 (q, J=7.4 Hz, 2H), 2.16–2.03 (m, 1H), 1.56–0.67 (m, 11H); $^{13}$C NMR (75 MHz,CDCl$_3$) δ173.7, 168.0, 149.6, 141.1, 126.0, 124.3, 121.4, 121.0, 116.8, 44.5, 22.3, 21.5, 17.5, 17.1, 14.8, 13.5, 11.1, 7.32; MS(ESI) 283(M–H)$^+$.

EXAMPLE 81

N-{[(1R,2R)-2-(2-Ethylbenzoxazol-7-yl)cyclopropyl]methyl}(ethylamino)carboxamide The title compound was prepared by the general procedure described in Example 12, using 15a (86 mg) and ethyl isocyanate (71 mg). Purification by flash chromatography over silica gel (elution with 80% ethyl acetate) gave 280 mg (90%) of the desired product.

IR (film, cm$^{-1}$) 3347, 1655; $^{13}$C NMR (75 MHz,CDCl$_3$) δ167.1, 157.9, 148.6, 140.2, 125.4, 123.4, 120.3, 115.7, 43.6, 34.4, 21.4, 21.3, 16.2, 14.8, 12.8, 10.2; MS(ESI) 286(M−H)$^+$.

EXAMPLE 82

N-{[(1R,2R)-2-(2-Propylbenzoxazol-7-yl)cyclopropyl]methyl}acetamide

The title compound was prepared by the general procedure described in Example 7, using 15b (115 mg), Et$_3$N (101 mg) and acetyl chloride (39 mg). Purification by flash chromatography over silica gel, elution with 50% EtOAc/hexanes, gave 117 mg (86%) of desired product.

$^1$H NMR (300 MHz, CDCl$_3$) δ7.42 (d, J=7.9 Hz, 1H), 7.13 (t, J=7.8 Hz, 1H), 6.85 (d, J=7.6 Hz, 1H), 6.28 (br, s, 1H), 3.48–3.39 (m, 1H), 3.23–3.13 (m, 1H), 2.86 (t, J=7.5 Hz, 2H), 2.07–2.00 (m, 1H), 1.98 (s, 3H), 1.95–1.83 (m, 2H), 1.59–1.50 (m, 1H), 1.23–1.14 (m, 1H), 1.03–0.96 (m, 4H); $^{13}$C NMR (75 MHz, CDCl$_3$) δ170.2, 166.8, 149.3, 140.9, 125.7, 124.1, 121.3, 116.6, 43.7, 36.6, 30.4, 21.2, 20.2, 14.1, 13.7, 13.2; MS (ESI): 273 (M+H)$^+$.

EXAMPLE 83

N-({(1R,2R)-2-[2-(Methylethyl)benzoxazol-7-yl]cyclopropyl}methyl)acetamide

The title compound was prepared by the general procedure described in Example 7, using 15c (115 mg), Et$_3$N (101 mg) and acetyl chloride (39 mg). Purification by flash chromatography over silica gel, elution with 50% EtOAc/hexanes, gave 126 mg (93%) of desired product.

$^1$H NMR (300 MHz, CDCl$_3$) δ7.45 (d, J=7.9 Hz, 1H), 7.15 (t, J=7.8 Hz, 1H), 6.86 (d, J=7.4 Hz, 1H), 6.10 (br, s, 1H), 3.59–3.40 (m, 1H), 3.27–3.16 (m, 2H), 2.10–2.02 (m, 1H), 1.99 (s, 3H), 1.59–1.50 (m, 1H), 1.45 (d, J=7.0 Hz, 6H), 1.24–1.16 (m, 1H), 1.05–0.96 (m, 1H); $^{13}$C NMR (75 MHz, CDCl$_3$) δ171.0, 170.2, 149.2, 140.8, 125.7, 124.0, 121.3, 116.7, 43.7, 36.6, 28.2, 21.2, 20.3, 17.2, 13.2; MS (ESI): 273 (M+H)$^+$.

EXAMPLE 84

N-{[(1R,2R)-2-(2-Propylbenzoxazol-7-yl)cyclopropyl]methyl}propanamide

The title compound was prepared by the general procedure described in Example 12, using 15b (115 mg), Et$_3$N (101 mg) and propionyl chloride (46 mg). Purification by flash chromatography over silica gel, elution with 30% EtOAc/hexanes, gave 112 mg (78%) of desired product.

$^1$H NMR (300 MHz, CDCl$_3$) δ7.44 (d, J=7.9 Hz, 1H), 7.16 (t, J=7.8 Hz, 1H), 6.86 (d, J=7.6 Hz, 1H), 5.99 (br, s, 1H), 3.51–3.42 (m, 1H), 3.26–3.17 (m, 1H), 2.88 (t, J=7.6 Hz, 2H), 2.22 (q, J=7.6 Hz, 2H), 2.11–2.03 (m, 1H), 1.97–1.84 (m, 2H), 1.58–1.47 (m, 1H), 1.25–1.13 (m, 4H), 1.08–0.97 (m, 4H); $^{13}$C NMR (75 MHz, CDCl$_3$) δ173.7, 166.8, 149.3, 141.0, 125.7, 124.3, 121.2, 116.7, 43.5, 30.5, 29.6, 21.3, 20.2, 17.1, 13.7, 9.8; MS (ESI): 287 (M+H)$^+$.

EXAMPLE 85

N-({(1R,2R)-2-[2-(Methylethyl)benzoxazol-7-yl]cyclopropyl}methyl)propanamide

The title compound was prepared by the general procedure described in Example 7, using 15c (115 mg), Et$_3$N (101 mg) and propionyl chloride (46 mg). Purification by flash chromatography over silica gel, elution with 30% EtOAc/hexanes, gave 121 mg (85%) of desired product.

$^1$H NMR (300 MHz, CDCl$_3$) δ7.42 (d, J=7.9 Hz, 1H), 7.13 (t, J=7.8 Hz, 1H), 6.83 (d, J=7.5 Hz, 1H), 6.15 (br, s, 1H), 3.47–3.38 (m, 1H), 3.26–3.14 (m, 2H), 2.19 (q, J=7.6 Hz, 2H), 2.11–2.03 (m, 1H), 1.57–1.49 (m, 1H), 1.42 (d, J=7.0 Hz, 6H), 1.22–1.10 (m, 4H), 1.02–0.94 (m, 1H); $^{13}$C NMR (75 MHz, CDCl$_3$) δ173.8, 170.9, 149.2, 140.9, 125.8, 124.0, 121.2, 116.7, 43.5, 29.6, 28.8, 21.3, 20.3, 17.1, 13.2, 9.8; MS (ESI): 287 (M+H)$^+$.

EXAMPLE 86

N-{[(1R,2R)-2-(2-Propylbenzoxazol-7-yl)cyclopropyl]methyl}butanamide

The title compound was prepared by the general procedure described in Example 7, using 15b (115 mg), Et$_3$N (101 mg) and butyryl chloride (53 mg). Purification by flash chromatography over silica gel, elution with 30% EtOAc/hexanes, gave 113 mg (75%) of desired product.

$^1$H NMR (300 MHz, CDCl$_3$) δ7.41 (d, J=7.9 Hz, 1H), 7.13 (t, J=7.8 Hz, 1H), 6.84 (d, J=7.4 Hz, 1H), 6.16 (br, s, 1H), 3.48–3.39 (m, 1H), 3.25–3.16 (m, 1H), 2.85 (t, J=7.5 Hz, 2H), 2.15 (t, J=7.5 Hz, 2H), 2.08–2.02 (m, 1H), 1.93–1.81 (m, 2H), 1.69–1.57 (m, 2H), 1.54–1.47 (m, 1H), 1.20–1.13 (m, 1H), 1.05–0.87 (m, 7H); $^{13}$C NMR (75 MHz, CDCl$_3$) δ173.0, 166.7, 149.3, 141.0, 125.7, 124.0, 121.2, 116.6, 43.4, 38.6, 30.4, 21.3, 20.2, 19.1, 17.1, 13.6, 13.2; MS (ESI): 301 (M+H)$^+$.

EXAMPLE 87

N-({(1R,2R)-2-[2-(Methylethyl)benzoxazol-7-yl]cyclopropyl}methyl)butanamide

The title compound was prepared by the general procedure described in Example 7, using 15c (115 mg), Et$_3$N (101 mg) and butyryl chloride (53 mg). Purification by flash chromatography over silica gel, elution with 30% EtOAc/hexanes, gave 108 mg (72%) of desired product.

$^1$H NMR (300 MHz, CDCl$_3$) δ7.44 (d, J=7.9 Hz, 1H), 7.14 (t, J=7.8 Hz, 1H), 6.85 (d, J=7.6 Hz, 1H), 6.02 (br, s, 1H), 3.48–3.40 (m, 1H), 3.27–3.16 (m, 2H), 2.15 (t, J=7.3 Hz, 2H), 2.10–2.03 (m, 1H), 1.70–1.58 (m, 2H), 1.57–1.49 (m, 1H), 1.44 (d, J=7.0 Hz, 6H), 1.25–1.15 (m, 1H), 1.03–0.94 (m, 1H), 0.91 (t, J=7.4 Hz, 3H); $^{13}$C NMR (75 MHz, CDCl$_3$) δ172.9, 170.9, 149.2, 140.9, 125.7, 124.0, 121.2, 116.7, 43.4, 38.6, 28.8, 21.3, 20.3, 19.1, 17.1, 13.6, 13.2; MS (ESI): 301 (M+H)$^+$.

EXAMPLE 88

N-{[(1R,2R)-2-(2-Propylbenzoxazol-7-yl)cyclopropyl]methyl}-3-methylbutanamide

The title compound was prepared by the general procedure described in Example 7, using 15b (115 mg), Et$_3$N (101 mg) and iso-butyryl chloride (53 mg). Purification by flash chromatography over silica gel, elution with 30% EtOAc/hexanes, gave 107 mg (71%) of desired product.

$^1$H NMR (300 MHz, CDCl$_3$) δ7.44 (d, J=7.9 Hz, 1H), 7.17 (t, J=7.8 Hz, 1H), 6.86 (d, J=7.6 Hz, 1H), 6.00 (br, s, 1H), 3.48–3.39 (m, 1H), 3.26–3.17 (m, 1H), 2.87 (t, J=7.4 Hz, 2H), 2.42–2.29 (m, 1H), 2.10–2.01 (m, 1H), 1.94–1.82 (m, 2H), 1.57–1.46 (m, 1H), 1.24–1.10 (m, 7H), 1.06–0.97 (m, 4H); $^{13}$C NMR (75 MHz, CDCl$_3$) δ176.9, 166.7, 149.4, 141.0, 125.7, 124.0, 121.2, 116.6, 43.4, 35.6, 30.5, 21.3, 20.2, 19.6, 17.0, 13.7, 13.1; MS (ESI): 301 (M+H)+.

EXAMPLE 89

N-({(1R,2R)-2-[2-(Methylethyl)benzoxazol-7-yl]cyclopropyl}methyl)-3-methylbutanamide The title compound was prepared by the general procedure described in Example 7, using 15c (115 mg), Et$_3$N (101 mg) and iso-butyryl chloride (53 mg). Purification by flash chromatography over silica gel, elution with 30% EtOAc/hexanes, gave 115 mg (77%) of desired product.

$^1$H NMR (300 MHz, CDCl$_3$) δ7.43 (d, J=7.9 Hz, 1H), 7.13 (t, J=7.8 Hz, 1H), 6.84 (d, J=7.6 Hz, 1H), 6.06 (br, s, 1H), 3.45–3.37 (m, 1H), 3.28–3.16 (m, 2H), 2.42–2.27 (m, 1H), 2.10–2.03 (m, 1H), 1.58–1.48 (m, 1H), 1.43 (d, J=7.0 Hz, 6H), 1.23–1.08 (m, 7H), 1.03–0.95 (m, 1H); $^{13}$C NMR (75 MHz, CDCl$_3$) δ177.0, 170.9, 149.3, 140.9, 125.8, 124.0, 121.2, 116.7, 43.3, 35.5, 28.8, 21.3, 20.3, 19.6, 17.0, 13.2; MS (ESI): 301 (M+H)+.

EXAMPLE 90

N-{[(1R,2R)-2-(2-Propylbenzoxazol-7-yl)cyclopropyl]methyl}cyclopropylcarboxamide The title compound was prepared by the general procedure described in Example 11, using 15b (115 mg), Et$_3$N (101 mg) and cyclopropane carbonyl chloride (52 mg). Purification by flash chromatography over silica gel, elution with 30% EtOAc/hexanes, gave 112 mg (75%) of desired product.

$^1$H NMR (300 MHz, CDCl$_3$) δ7.42 (d, J=7.9 Hz, 1H), 7.14 (t, J=7.8 Hz, 1H), 6.84 (d, J=7.6 Hz, 1H), 6.45 (br, s, 1H), 3.51–3.42 (m, 1H), 3.26–3.17 (m, 1H), 2.86 (t, J=7.4 Hz, 2H), 2.09–2.01 (m, 1H), 1.94–1.82 (m, 2H), 1.59–1.48 (m, 1H), 1.42–1.33 (m, 1H) 1.21–1.14 (m, 1H), 1.05–0.92 (m, 6H) 0.70–0.64 (m, 2H); $^{13}$C NMR (75 MHz, CDCl$_3$) δ173.5, 166.8, 149.3, 141.0, 125.8, 124.0, 121.2, 116.6, 43.7, 30.4, 29.5, 21.3, 20.2, 17.1, 14.6, 13.3, 7.0; MS (ESI): 299 (M+H)+.

EXAMPLE 91

N-({(1R,2R)-2-[2-(Methylethyl)benzoxazol-7-yl]cyclopropyl}methyl)cyclopropylcarboxamide The title compound was prepared by the general procedure described in Example 11, using 15c (115 mg), Et$_3$N (101 mg) and cyclopropane carbonyl chloride (52 mg). Purification by flash chromatography over silica gel, elution with 30% EtOAc/hexanes, gave 114 mg (77%) of desired product.

$^1$H NMR (300 MHz, CDCl$_3$) δ7.45 (d, J=7.9 Hz, 1H), 7.14 (t, J=7.8 Hz, 1H), 6.86 (d, J=7.6 Hz, 1H), 6.32 (br, s, 1H), 3.52–3.42 (m, 1H), 3.28–3.17 (m, 2H), 2.11–2.04 (m, 1H), 1.61–1.50 (m, 1H), 1.44 (d, J=6.9 Hz, 6H), 1.42–1.33 (m, 1H), 1.22–1.16 (m, 1H), 1.04–0.93 (m, 3H), 0.73–0.67 (m, 2H); $^{13}$C NMR (75 MHz, CDCl$_3$) δ173.5, 170.9, 149.2, 140.9, 125.8, 124.0, 121.2, 116.7, 43.8, 28.8, 21.3, 20.3, 17.1, 14.6, 13.3, 7.0; MS (ESI): 299 (M+H)+.

EXAMPLE 92

N-{[(1R,2R)-2-(2-Propylbenzoxazol-7-yl)cyclopropyl]methyl}(ethylamino)carboxamide The title compound was prepared by the general procedure described in Example 12, using 15b (115 mg), ethyl isocyanate (35 mg). Purification by flash chromatography over silica gel, elution with 50% EtOAc/hexanes, gave 107 mg (71%) of desired product.

$^1$H NMR (300 MHz, CDCl$_3$) δ7.42 (d, J=7.9 Hz, 1H), 7.13 (t, J=7.8 Hz, 1H), 6.83 (d, J=7.6 Hz, 1H), 5.17 (br, s, 1H), 4.88 (br, s, 1H), 3.39–3.31 (m, 1H), 3.23–3.12 (m, 3H), 2.86 (t, J=7.4 Hz, 2H), 2.07–2.00 (m, 1H), 1.94–1.81 (m, 2H), 1.60–1.49 (m, 1H), 1.17–0.93 (m, 8H); $^{13}$C NMR (75 MHz, CDCl$_3$) δ166.8, 158.4, 149.2, 141.0, 126.0, 124.0, 121.0, 116.4, 44.4, 35.1, 30.4, 21.9, 20.2, 16.9, 15.4, 13.7, 13.4; MS (ESI): 302 (M+H)+.

EXAMPLE 93

N-({(1R,2R)-2-[2-(Methylethyl)benzoxazol-7-yl]cyclopropyl}methyl)(ethylamino)carboxamide The title compound was prepared by the general procedure described in Example 12, using 15c (115 mg), ethyl isocyanate (35 mg). Purification by flash chromatography over silica gel, elution with 50% EtOAc/hexanes, gave 118 mg (79%) of desired product.

$^1$H NMR (300 MHz, CDCl$_3$) δ7.40 (d, J=7.9 Hz, 1H), 7.09 (t, J=7.8 Hz, 1H), 6.80 (d, J=7.3 Hz, 1H), 5.49 (br, s, 1H), 5.23 (br, s, 1H), 3.22–3.10 (m, 5H), 2.04–1.98 (m, 1H), 1.59–1.48 (m, 1H), 1.41 (d, J=6.9 Hz, 6H), 1.23–1.02 (m, 4H), 0.98–0.91 (m, 1H); $^{13}$C NMR (75 MHz, CDCl$_3$) δ171.0, 158.7, 149.1, 140.8, 126.1, 124.0, 121.1, 116.4, 44.3, 35.0, 28.8, 21.9, 20.2, 16.9, 15.4, 13.4; MS (ESI): 302 (M+H)+.

EXAMPLE 94

N-({(1R,2R)-2-[2-(5-Phenylbutyl)benzoxazol-7-yl]cyclopropyl}methyl)acetamide

The title compound was prepared by the general procedure described in Example 7, using 15d (80 mg), Et$_3$N (51 mg) and acetyl chloride (22 mg). Purification by flash chromatography over silica gel, elution with 50% EtOAc/hexanes, gave 46 mg (51%) of desired product.

$^1$H NMR (300 MHz, CDCl$_3$) δ7.46 (d, J=7.7 Hz, 1H), 7.32–7.26 (m, 2H), 7.20–7.15 (m, 4H), 7.88 (d, J=7.6 Hz, 1H), 5.92 (br, s, 1H), 3.51–3.42 (m, 1H), 3.24–3.15 (m, 1H), 2.95 (t, J=7.3 Hz, 2H), 2.70 (t, J=7.6 Hz, 2H), 2.10–2.03 (m, 1H), 1.99 (s, 3H), 1.99–1.89 (m, 2H), 1.83–1.73 (m, 2H), 1.58–1.47 (m, 1H), 1.26–1.17 (m, 1H), 1.03–0.98 (m, 1H); $^{13}$C NMR (75 MHz, CDCl$_3$) δ170.0, 166.7, 149.4, 141.9, 141.1, 128.3, 125.8, 124.1, 121.3, 116.8, 43.7, 35.4, 30.8, 28.5, 26.4, 23.2, 21.2, 17.2, 13.2; MS (ESI): 363 (M+H)+.

EXAMPLE 95

N-({(1R,2R)-2-[2-(5-Phenylbutyl)benzoxazol-7-yl]cyclopropyl}methyl)propanamide

The title compound was prepared by the general procedure described in Example 7, using 15d (80 mg), Et$_3$N (51 mg) and propionyl chloride (25 mg). Purification by flash chromatography over silica gel, elution with 30% EtOAc/hexanes, gave 59 mg (63%) of desired product.

$^1$H NMR (300 MHz, CDCl$_3$) δ7.47 (d, J=7.8 Hz, 1H), 7.30–7.26 (m, 2H), 7.20–7.16 (m, 4H), 6.89 (d, J=7.6 Hz, 1H), 5.86 (br, s, 1H), 3.52–3.43 (m, 1H), 3.28–3.19 (m, 1H), 2.95 (t, J=7.3 Hz, 2H), 2.70 (t, J=7.6 Hz, 2H), 2.22 (q, J=7.6 Hz, 2H), 2.10–2.03 (m, 1H), 1.99–1.90 (m, 2H), 1.83–1.73 (m, 2H), 1.59–1.49 (m, 1H), 1.25–1.14 (m, 4H), 1.05–0.98 (m, 1H); $^{13}$C NMR (75 MHz, CDCl$_3$) δ173.7, 166.7, 149.4, 141.9, 141.0, 128.3, 125.8, 124.1, 121.3, 116.7, 43.6, 35.4, 30.8, 29.6, 28.5, 26.4, 21.3, 17.1, 13.2, 9.8; MS (ESI): 377 (M+H)+.

EXAMPLE 96

N-({(1R,2R)-2-[2-(5-Phenylbutyl)benzoxazol-7-yl]cyclopropyl}methyl)butanamide

The title compound was prepared by the general procedure described in Example 7, using 15d (80 mg), Et₃N (51 mg) and butyryl chloride (29 mg). Purification by flash chromatography over silica gel, elution with 30% EtOAc/hexanes, gave 43 mg (44%) of desired product.

¹H NMR (300 MHz, CDCl₃) 7.46 (d, J=7.8 Hz, 1H), 7.30–7.26 (m, 2H), 7.20–7.16 (m, 4H), 6.89 (d, J=7.5 Hz, 1H), 5.85 (br, s, 1H), 3.51–3.42 (m, 1H), 3.28–3.19 (m, 1H), 2.95 (t, J=7.3 Hz, 2H), 2.70 (t, J=7.6 Hz, 2H), 2.17 (t, J=7.3 Hz, 2H), 2.11–2.05 (m, 1H), 2.00–1.90 (m, 2H), 1.83–1.73 (m, 2H), 1.72–1.62 (m, 2H), 1.59–1.48 (m, 1H), 1.24–1.17 (m, 1H), 1.04–0.98 (m, 1H), 0.94 (t, J=7.3 Hz, 3H); ¹³C NMR (75 MHz, CDCl₃) 172.9, 166.7, 149.4, 141.9, 141.0, 128.3, 125.8, 124.1, 121.3, 116.7, 43.5, 38.7, 35.4, 30.8, 28.5, 26.4, 21.3, 19.1, 17.1, 13.7, 13.2; MS (ESI): 391 (M+H)+.

EXAMPLE 97

N-({(1R,2R)-2-[2-(5-Phenylbutyl)benzoxazol-7-yl]cyclopropyl}methyl)-2-methylpropanamide The title compound was prepared by the general procedure described in Example 7, using 15d (80 mg), Et₃N (51 mg) and iso-butyryl chloride (29 mg). Purification by flash chromatography over silica gel, elution with 30% EtOAc/hexanes, gave 55 mg (57%) of desired product.

¹H NMR (300 MHz, CDCl₃) δ7.47 (d, J=7.8 Hz, 1H), 7.30–7.26 (m, 2H), 7.20–7.16 (m, 4H), 6.89 (d, J=7.6 Hz, 1H), 5.86 (br, s, 1H), 3.51–3.42 (m, 1H), 3.29–3.20 (m, 1H), 2.96 (t, J=7.3 Hz, 2H), 2.70 (t, J=7.6 Hz, 2H), 2.42–2.32 (m, 1H), 2.11–2.05 (m, 1H), 1.99–1.90 (m, 2H), 1.82–1.72 (m, 2H), 1.59–1.49 (m, 1H), 1.25–1.14 (m, 7H), 1.06–0.99 (m, 1H); ¹³C NMR (75 MHz, CDCl₃) δ177.0, 166.7, 149.4, 141.9, 141.0, 128.3, 125.8, 124.1, 121.3, 116.7, 43.4, 35.6, 35.4, 30.8, 28.5, 26.4, 21.3, 19.6, 17.0, 13.1.

EXAMPLE 98

N-({(1R,2R)-2-[2-(5-Phenylbutyl)benzoxazol-7-yl]cyclopropyl}methyl)cyclopropylcarboxamide The title compound was prepared by the general procedure described in Example 11, using 15d (80 mg), Et₃N (51 mg) and cyclopropane carbonyl chloride (29 mg). Purification by flash chromatography over silica gel, elution with 25% EtOAc/hexanes, gave 25 mg (26%) of desired product.

¹H NMR (300 MHz, CDCl₃) δ7.47 (d, J=7.8 Hz, 1H), 7.31–7.26 (m, 2H), 7.21–7.16 (m, 4H), 6.89 (d, J=7.5 Hz, 1H), 6.06 (br, s, 1H), 3.54–3.45 (m, 1H), 3.29–3.20 (m, 1H), 2.96 (t, J=7.3 Hz, 2H), 2.70 (t, J=7.6 Hz, 2H), 2.10–2.05 (m, 1H), 2.00–1.90 (m, 2H), 1.83–1.73 (m, 2H), 1.66–1.51(m, 1H), 1.39–1.32 (m, 1H), 1.25–1.18 (m, 1H), 1.09–0.98 (m, 3H), 0.94–0.88 (m, 1H), 0.79–0.72 (m, 1H); ¹³C NMR (75 MHz, CDCl₃) δ173.5, 166.8, 149.4, 141.9, 141.0, 128.3, 125.8, 124.1, 121.3, 116.7, 43.8, 35.4, 30.8, 28.5, 26.4, 21.3, 17.1, 14.7, 13.3, 8.76, 7.08.

What is claimed is:
1. A compound of Formula I:

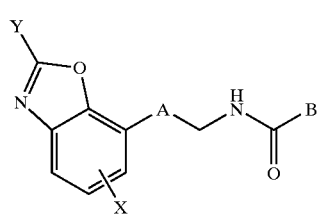

(I)

or a pharmaceutically acceptable salt or solvate thereof wherein
A is $C_{1-4}$ alkylene or 1,2 disubstituted cyclopropyl;
B is $C_{1-6}$ alkyl group, $C_{3-6}$ cycloalkyl group, $C_{1-6}$ alkoxy, or $C_{1-4}$ alkylamino;
X is hydrogen, halogen, $C_{2-4}$ alkenyl, $C_{1-6}$ alkyl, furyl, or phenyl optionally substituted with halogen, $C_{1-6}$ alkoxy, or haloalkyl; and
Y is hydrogen, phenyl, or $C_{1-6}$ alkyl group optionally substituted with phenyl.
2. The compound of claim 1 wherein A is $C_{1-4}$ alkylene; B is $C_{1-3}$ alkyl group, $C_3$ cycloalkyl group, $C_{1-4}$ alkoxy or $C_{1-4}$ alkylamino; X is hydrogen, halogen, $C_{2-4}$ alkenyl, $C_{1-2}$ alkyl, furyl, or phenyl optionally substituted with halogen, $C_{1-2}$ alkoxy, or haloalkyl; and Y is hydrogen, phenyl, or $C_{1-4}$ alkyl group optionally substituted with phenyl.
3. The compound of claim 2 wherein A is ethylene.
4. The compound of claim 2 wherein X is hydrogen selected from the group consisting of
N-[3-(2-methylbenzoxazol-7-yl)propyl]propanamide;
N-[3-(2-methylbenzoxazol-7-yl)propyl]butanamide;
cyclopropyl-N-[3-(2-methylbenzoxazol-7-yl)propyl]carboxamide;
2-methyl-N-[3-(2-methylbenzoxazol-7-yl)propyl]propanamide;
N-[3-(2-ethylbenzoxazol-7-yl)propyl]propanamide;
N-[3-(2-ethylbenzoxazol-7-yl)propyl]butanamide;
cyclopropyl-N-[3-(2-ethylbenzoxazol-7-yl)propyl]carboxamide;
N-{3-[2-(4-phenylbutyl)benzoxazol-7-yl]propyl}acetamide;
N-{3-[2-(4-phenylbutyl)benzoxazol-7-yl]propyl}propanamide;
N-{3-[2-(4-phenylbutyl)benzoxazol-7-yl]propyl}butanamide;
2-methyl-N-{3-[2-(4-phenylbutyl)benzoxazol-7-yl]propyl}propanamide;
cyclopropyl-N-{3-[2-(4-phenylbutyl)benzoxazol-7-yl]propyl}carboxamide;
(ethylamino)-N-{3-[2-(4-phenylbutyl)benzoxazol-7-yl]propyl}carboxamide;
and N-(3-benzoxazol-7-ylpropyl)-2-methylpropanamide.
5. The compounds of claim 2 selected from the group consisting of
N-[3-(6-bromo-2-ethylbenzoxazol-7-yl)propyl]acetamide;
N-[3-(2-ethyl-6-vinylbenzoxazol-7-yl)propyl]acetamide;
cyclopropyl-N-[3-(2-ethyl-6-methylbenzoxazol-7-yl)propyl]carboxamide;
cyclopropyl-N-{3-[2-ethyl-6-(4-fluorophenyl)benzoxazol-7-yl]propyl}carboxamide;

N-{3-[2-ethyl-6-(4-methoxyphenyl)benzoxazol-7-yl]
propyl}acetamide;

N-[3-(2-ethyl-6-phenylbenzoxazol-7-yl)propyl]
acetamide;

cyclopropyl-N-[3-(2-ethyl-6-phenylbenzoxazol-7-yl)
propyl]carboxamide;

N-[3-(2-ethyl-6-(2-furyl)benzoxazol-7-yl)propyl]
acetamide; and cyclopropyl-N-[3-(2-ethyl-6-(2-furyl)benzoxazol-7-yl)
propyl]carboxamide.

6. The compound of claim 1 wherein A is 1,2 disubstituted cyclopropyl; B is $C_{1-6}$ alkyl group; X is hydrogen, halogen, $C_{2-4}$ alkenyl, $C_{1-2}$ alkyl, furyl, or phenyl optionally substituted with halogen, $C_{1-2}$ alkoxy, or haloalkyl; and Y is hydrogen, phenyl, or $C_{1-4}$ alkyl group optionally substituted with phenyl.

7. The compound of claim 6 wherein X is hydrogen.

8. The compound of claim 7 selected from the group consisting of

N-{[(1R,2R)-2-(2-ethylbenzoxazol-7-yl)cyclopropyl]
methyl}acetamide;

N-{[(1R,2R)-2-(2-ethylbenzoxazol-7-yl)cyclopropyl]
methyl}propanamide;

N-{[(1R,2R)-2-(2-ethylbenzoxazol-7-yl)cyclopropyl]
methyl}butanamide;

N-{[(1R,2R)-2-(2-ethylbenzoxazol-7-yl)cyclopropyl]
methyl}-2-methylpropanamide;

N-{[(1R,2R)-2-(2-ethylbenzoxazol-7-yl)cyclopropyl]
methyl}cyclopropylcarboxamide;

N-{[(1R,2R)-2-(2-ethylbenzoxazol-7-yl)cyclopropyl]
methyl}(ethylamino)carboxamide;

N-{[(1R,2R)-2-(2-propylbenzoxazol-7-yl)cyclopropyl]
methyl}acetamide;

N-({(1R,2R)-2-[2-(methylethyl)benzoxazol-7-yl]
cyclopropyl}methyl)acetamide;

N-{[(1R,2R)-2-(2-propylbenzoxazol-7-yl)cyclopropyl]
methyl}propanamide;

N-({(1R,2R)-2-[2-(methylethyl)benzoxazol-7-yl]
cyclopropyl}methyl)propanamide;

N-{[(1R,2 R)-2-(2-propylbenzoxazol-7-yl)cyclopropyl]
methyl}butanamide;

N-({(1R,2R)-2-[2-(methylethyl)benzoxazol-7-yl]
cyclopropyl}methyl)butanamide;

N-{[(1R,2R)-2-(2-propylbenzoxazol-7-yl)cyclopropyl]
methyl}-3-methylbutanamide;

N-({(1R,2R)-2-[2-(methylethyl)benzoxazol-7-yl]
cyclopropyl}methyl)-3-methylbutanamide;

N-{[(1R,2R)-2-(2-propylbenzoxazol-7-yl)cyclopropyl]
methyl}cyclopropylcarboxamide;

N-({(1R,2R)-2-[2-(methylethyl)benzoxazol-7-yl]
cyclopropyl}methyl)cyclopropylcarboxamide;

N-{[(1R,2R)-2-(2-propylbenzoxazol-7-yl)cyclopropyl]
methyl}(ethylamino)carboxamide;

N-({(1R,2R)-2-[2-(methylethyl)benzoxazol-7-yl]
cyclopropyl}methyl)(ethylamino)carboxamide;

N-({(1R,2R)-2-[2-(4-phenylbutyl)benzoxazol-7-yl]
cyclopropyl}methyl)acetamide;

N-({(1R,2R)-2-[2-(4-phenylbutyl)benzoxazol-7-yl]
cyclopropyl}methyl)propanamide;

N-({(1R,2R)-2-[2-(4-phenylbutyl)benzoxazol-7-yl]
cyclopropyl}methyl)butanamide;

N-({(1R,2R)-2-[2-(4-phenylbutyl)benzoxazol-7-yl]
cyclopropyl}methyl)-2-methylpropanamide; and N-({(1R,2R)-2-[2-(4-phenylbutyl)benzoxazol-7-yl]
cyclopropyl}methyl)cyclopropylcarboxamide.

9. A method of treating a circadian rhythm-related disorder in a mammal in need of such treatment comprising administering to the mammal a therapeutically effective amount of a compound as defined in claim 1.

10. A pharmaceutical composition for treating circadian rhythm-related disorders comprising a therapeutically effective amount of a compound as defined in claim 1 and a pharmaceutically acceptable carrier, adjuvant or diluent.

* * * * *